(12) United States Patent
Wustman

(10) Patent No.: US 9,675,627 B2
(45) Date of Patent: Jun. 13, 2017

(54) DOSING REGIMENS FOR TREATING AND/OR PREVENTING CEREBRAL AMYLOIDOSES

(71) Applicant: Amicus Therapeutics, Inc., Cranbury, NJ (US)

(72) Inventor: Brandon Alan Wustman, San Diego, CA (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

(21) Appl. No.: 14/684,967

(22) Filed: Apr. 13, 2015

(65) Prior Publication Data

US 2016/0008383 A1 Jan. 14, 2016

Related U.S. Application Data

(60) Provisional application No. 61/979,408, filed on Apr. 14, 2014.

(51) Int. Cl.
*A61K 31/445* (2006.01)
*A61K 31/70* (2006.01)
*A61K 9/00* (2006.01)

(52) U.S. Cl.
CPC ............ *A61K 31/70* (2013.01); *A61K 9/0053* (2013.01); *A61K 31/445* (2013.01)

(58) Field of Classification Search
None
See application file for complete search history.

(56) References Cited

U.S. PATENT DOCUMENTS

| 2005/0031651 A1 | 2/2005 | Gervais et al. |
| 2007/0021381 A1 | 1/2007 | Fan et al. |
| 2007/0066543 A1 | 3/2007 | Mahuran et al. |
| 2008/0009516 A1 | 1/2008 | Wustman |

FOREIGN PATENT DOCUMENTS

| WO | WO-2006/133446 | 12/2006 |
| WO | WO-2008/134628 | 11/2008 |
| WO | WO-2011/049787 | 10/2009 |
| WO | WO-2011/011181 | 1/2011 |

OTHER PUBLICATIONS

Gandy, et al., Annals of Neurology, 68:220, 228 (2010).*
Alzheimer's Drug Discovery Foundation Funds Amicus Therapeutics to Advance Pharmalogical Chaperone Technology, Amicus Therapeutics, Inc., retrieved from the Internet http://www.alzdisvoery.org/wp-content/uploads/2010/05/addf-amicus-press-release.pdf May 6, 2012, 2 pages.
PCT International Search Report in PCT/US2010/052351, mailed Nov. 25, 2010, 2 pages.
Supplemental European Search Report in EP10825421.0, mailed May 14, 2013, 8 pages.
Biffi, Alessandro, et al., Cerebral Amyloid Angiopathy: A Systematic Review, *J. Clin. Neurol.* vol. 7 2011, 1-9.
Cataldo, Anne M., et al., Lysosomal hydrolases of different classes are abnormally distributed in brains of patients with Alzheimer disease, *Proc. Natl. Acad. Sci.*, vol. 88 Dec. 1991, 10998-11002.
Ghiso, Jorge, et al., Cerebral Amyloid Angiopath and Alzheimer's Disease, *NIH Manuscript* vol. 61 (*Suppl.*) Jul. 8, 2010, S111-S124.
Hinek, et al., Lysosomal sialidase (muraminidase-1) is targeted to the cell surface in a Multiprotein complex that facilitates elastic fiber assembly, *Journal of Biological Chemistry* vol. 281 No. 6 2005, 3698-3710.
Keilani, Serene, et al., Lysosomal Dysfunction in a Mouse Model of Sandhoff Disease Leads to Accumulation of Ganglioside-Bound Amyloid-B Peptide, *The Journal of Neuroscience* Apr. 11, 2012, 5223-5236.
Knight, E. M., et al., Evidence that small molecule enhancement of B-hexosaminidase activity corrects the behavioral phenotype in Dutch APP E693Q mice through reduction of ganglioside-bound AB, *Molecular Psychiatry* 2014, 1-9.
Koren III, John, et al., Chaperone signalling complexes in Alzheimer's disease, *Journal of Cellular and Molecular Medicine* vol. 13 No. 4 Apr. 2009, 619-630.
Ringe, Dagmar, et al., What are pharmacological chaperones and why are they interesting?, *Journal of Biology* vol. 8 No. 9 2009, 80.
Yerbury, Justin J., et al., Extracellular chaperones modulate the effects of Alzheimer's patient cerebrospinal fluid on Abeta (1-42) toxicity and uptake, *Cell Stress & Chaperones* vol. 15 No. 1 Jan. 2010, 115-121.
Yuzwa, Scott A., et al., A potent mechanism-inspired O-GlcNAcase inhibitor that blocks phosphorylation of tau in vivo, *Nature Chemical Biology*, vol. 4, No. 8. Aug. 2008, 24 pages.
Non-Final Office Action in U.S. Appl. No. 13/501,586, dated Sep. 2, 2014, 11 pages.
Non-Final Office Action in U.S. Appl. No. 13/501,586, dated Feb. 26, 2014, 9 pages.
PCT International Search Report in PCT/US2015/0215733, dated Jul. 17, 2015, 10 pages.

* cited by examiner

*Primary Examiner* — Michael Barker
(74) *Attorney, Agent, or Firm* — Servilla Whitney LLC

(57) ABSTRACT

Described herein are dosing regimens and kits for the treatment and/or prevention of cerebral amyloidoses such as Alzheimer's disease (AD) and/or cerebral amyloid angiopathy (CAA).

16 Claims, 17 Drawing Sheets

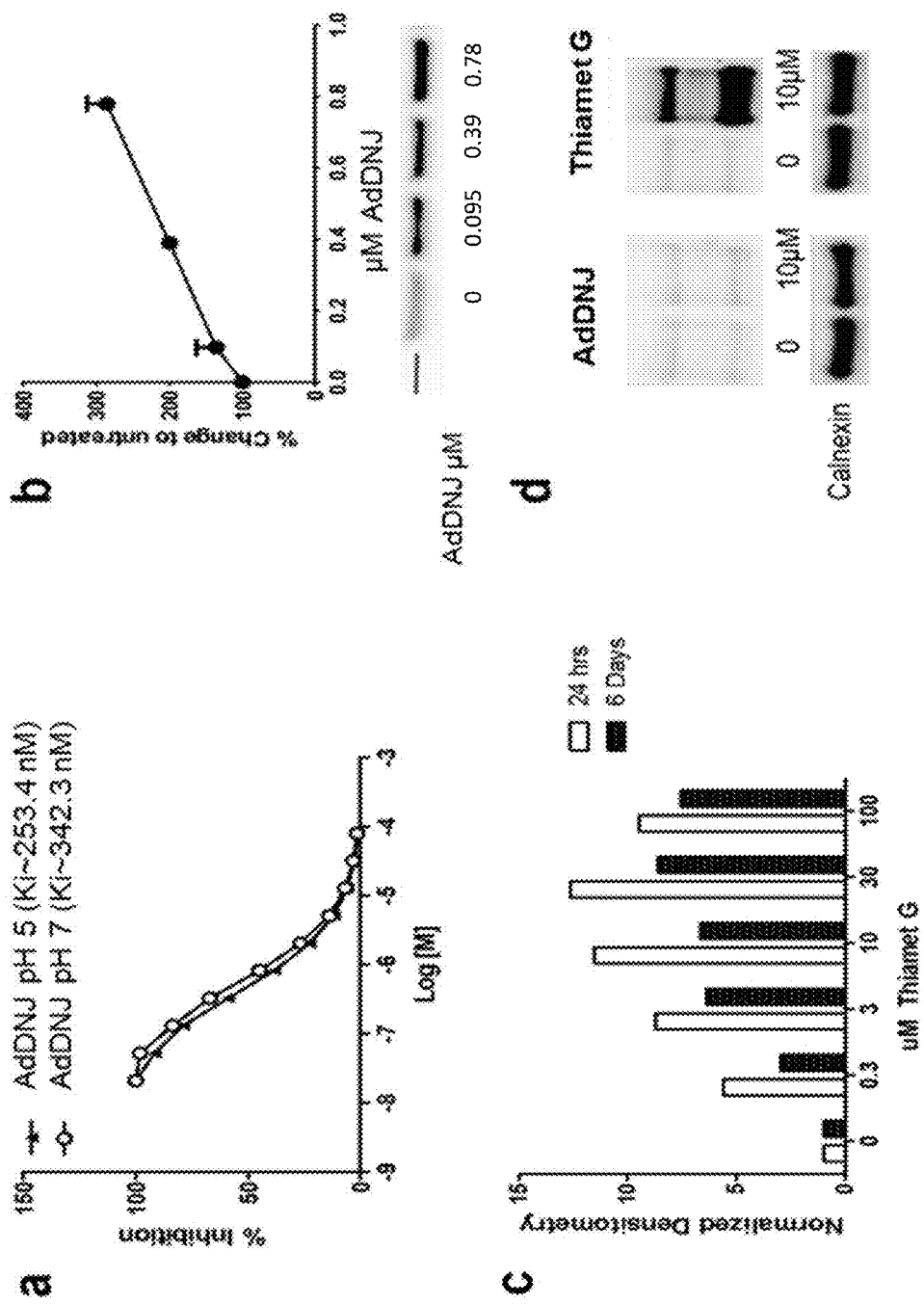
FIGS. 1 a-d

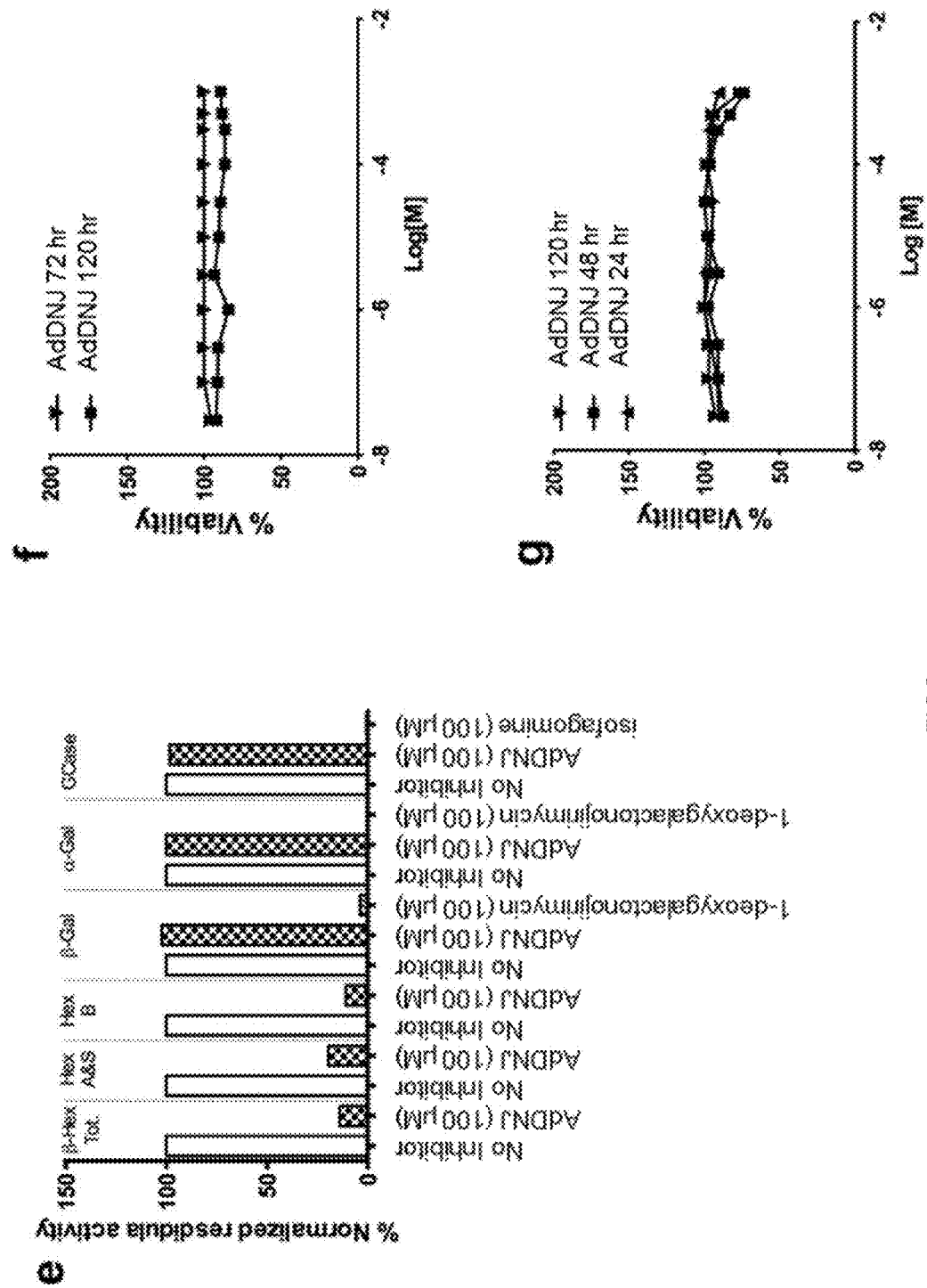
FIGS. 1 e-g

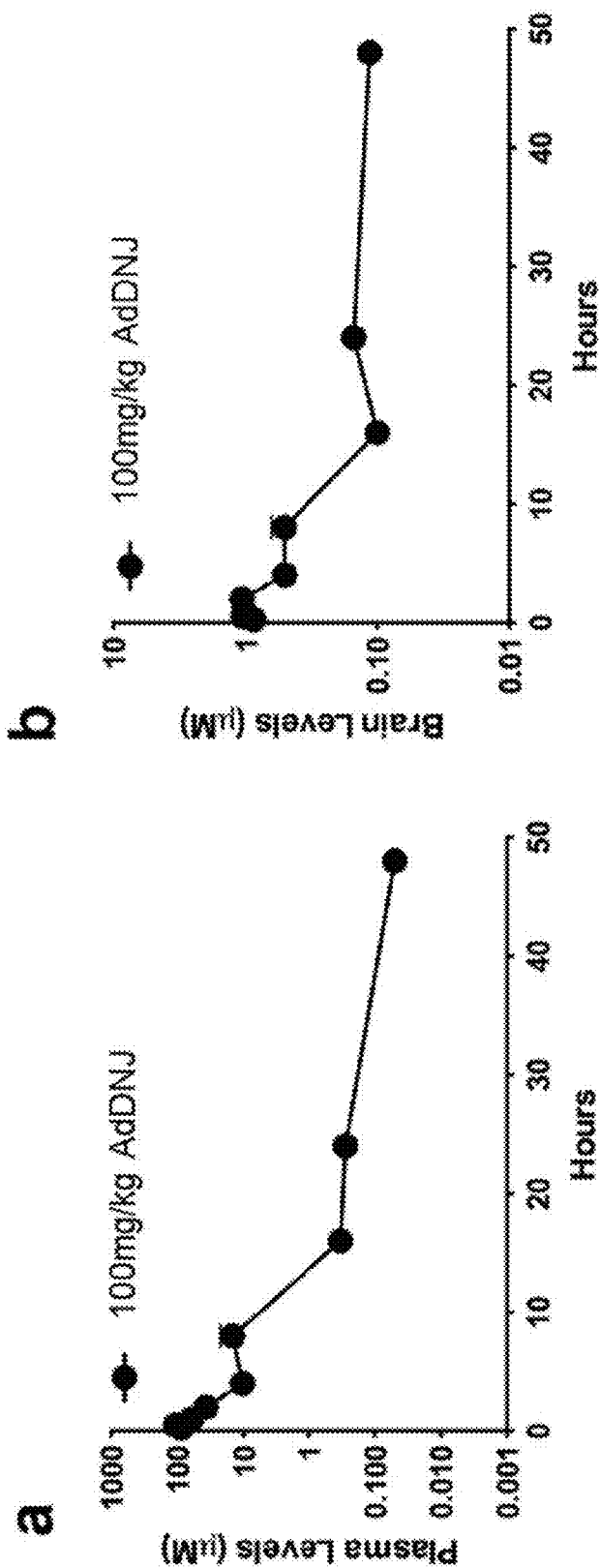
FIGS. 2 a-b

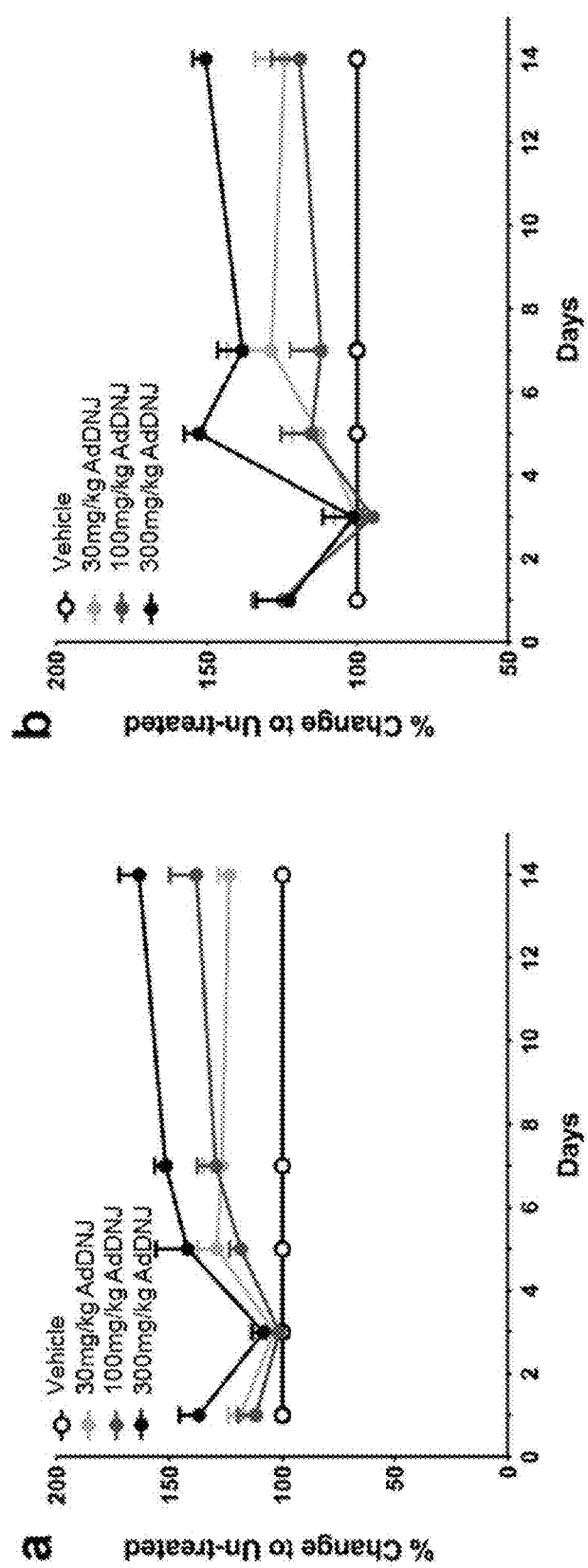
FIGS. 3 a-b

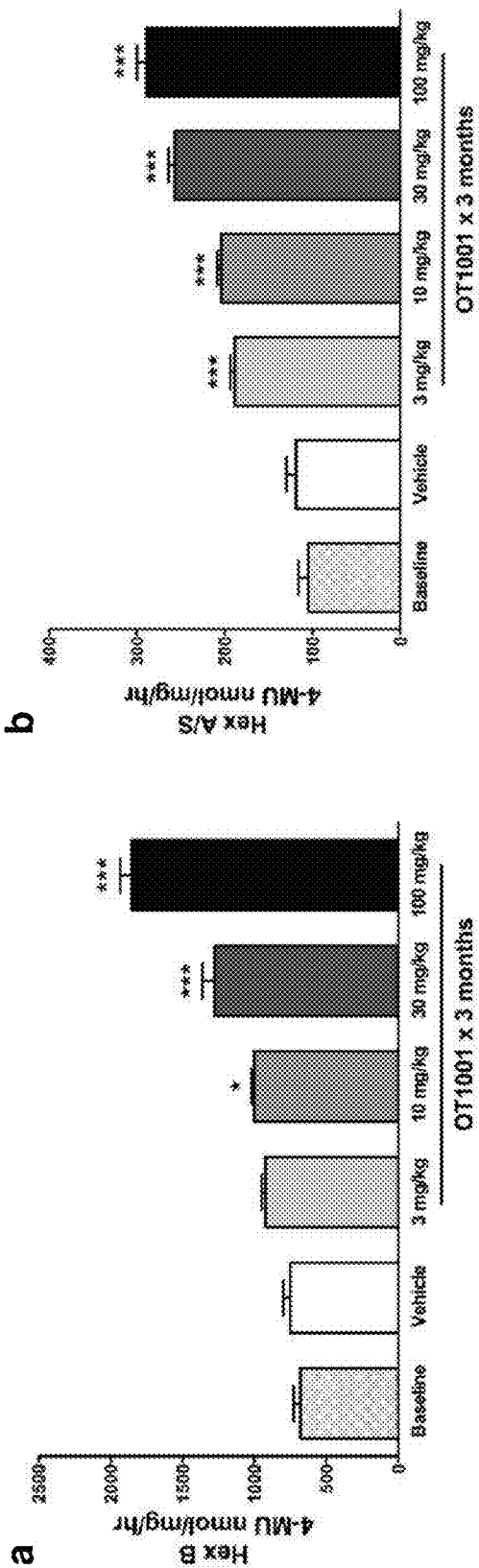
FIGS. 4 a-b

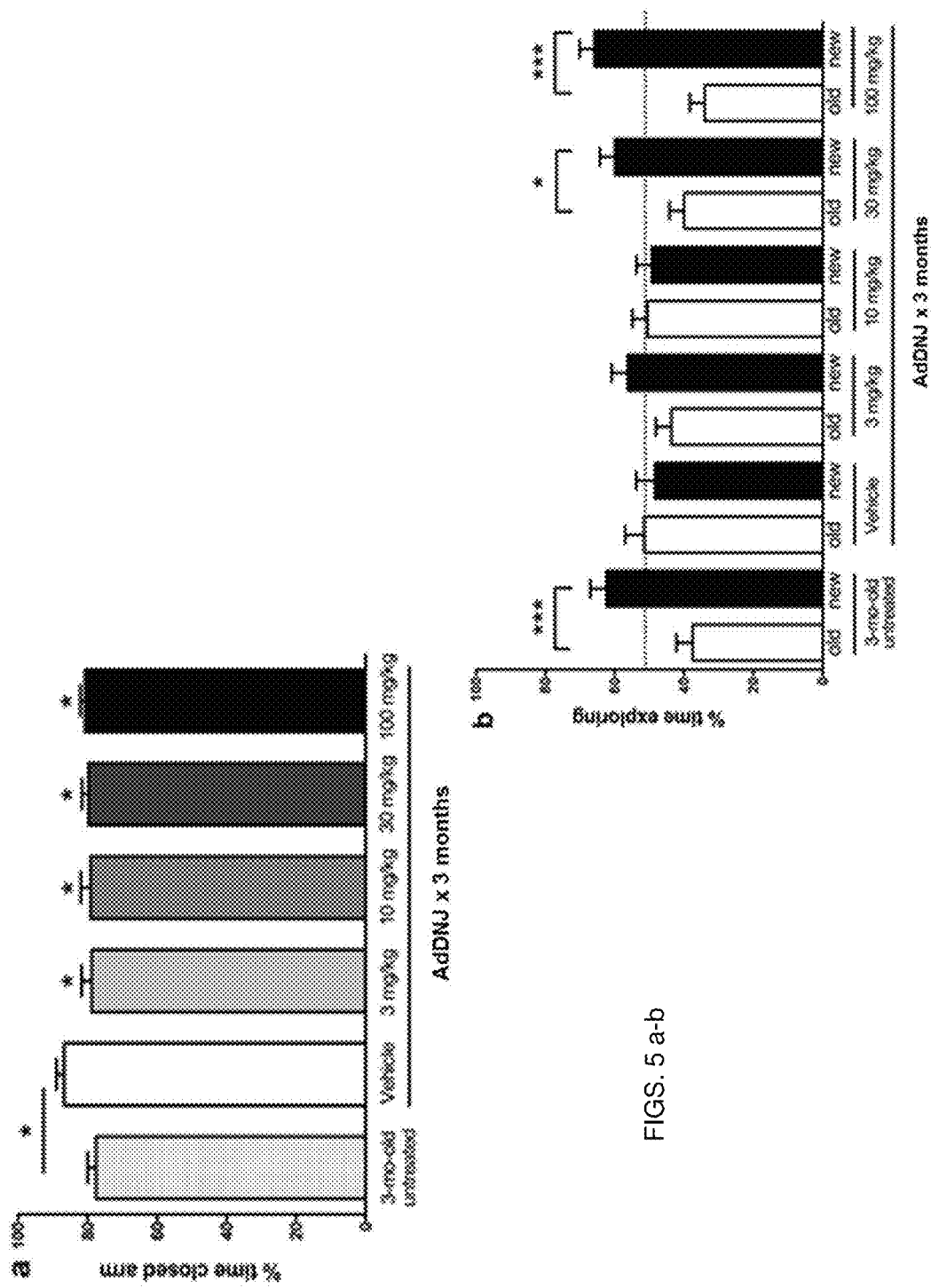
FIGS. 5 a-b

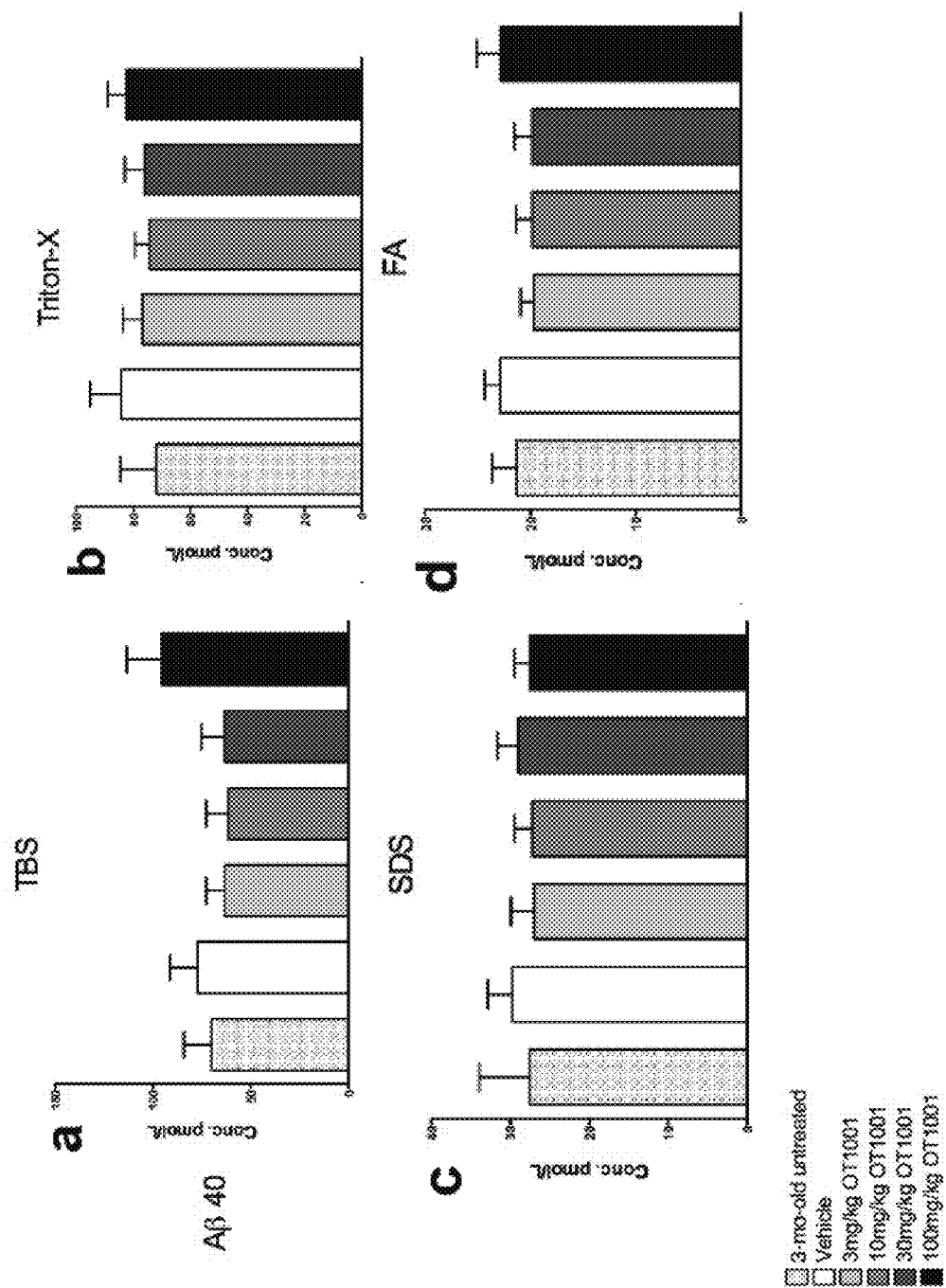
FIGS. 7 a-d

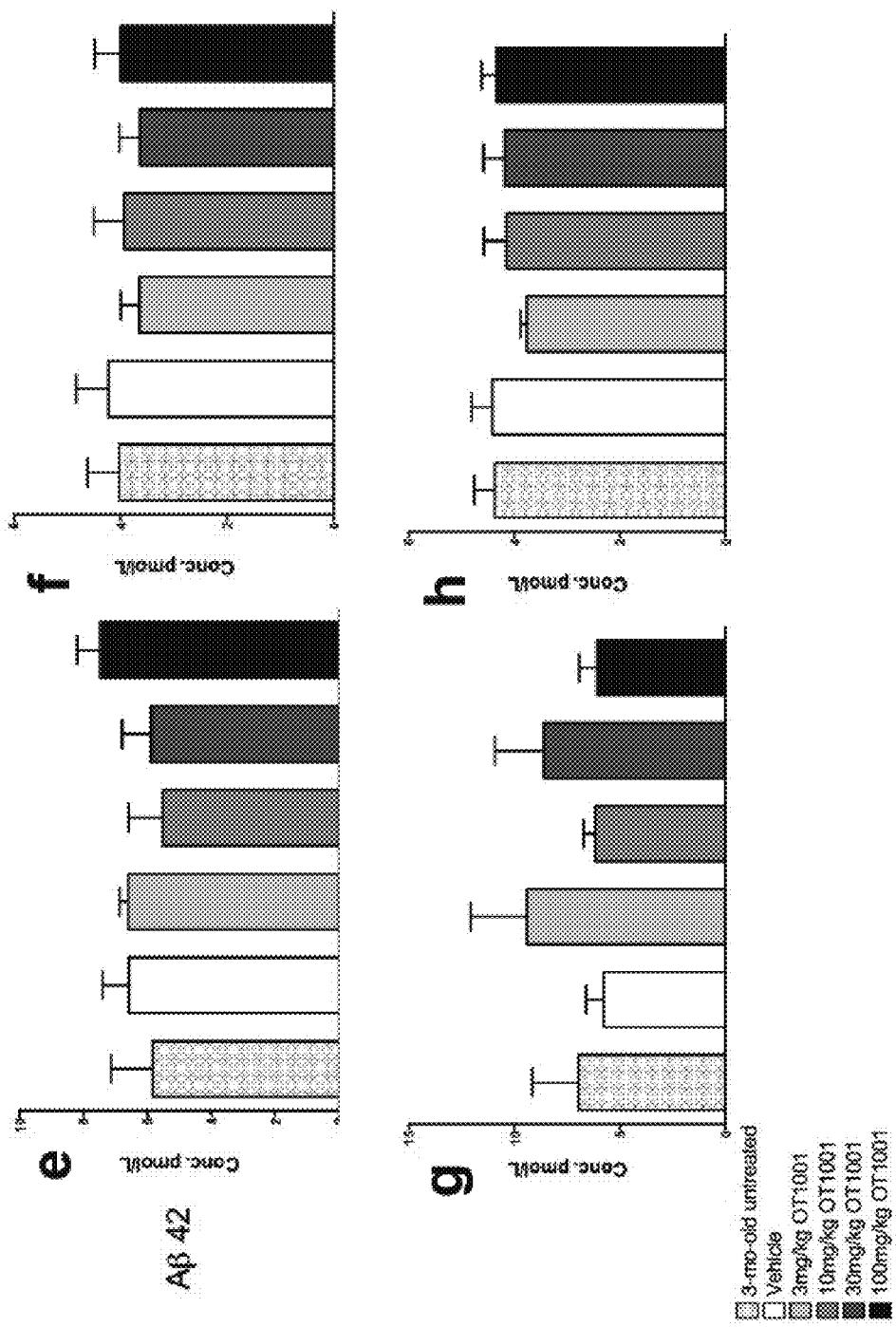
FIGS. 7 e-h

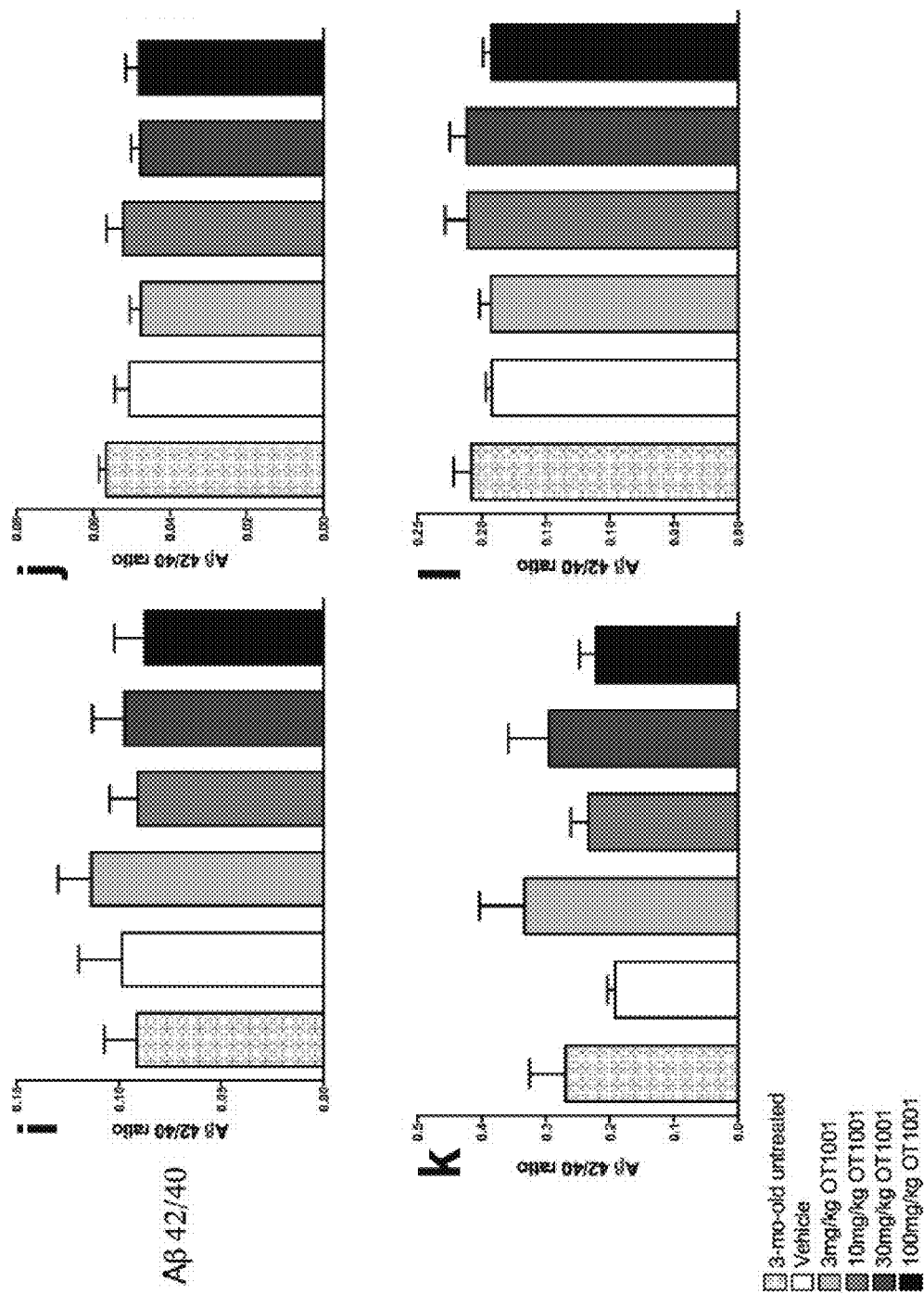
FIGS. 7 i-l

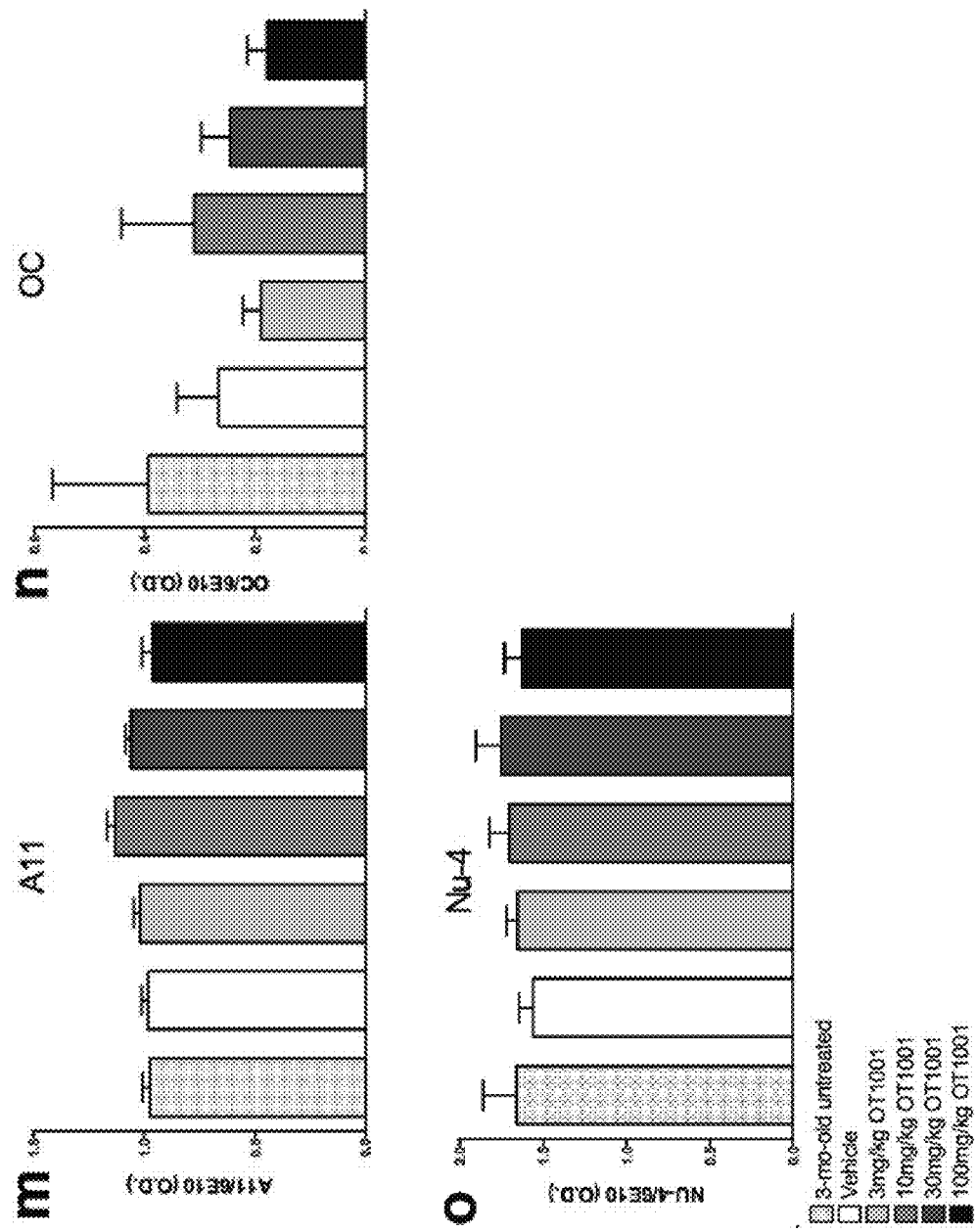
FIGS. 7 m-o

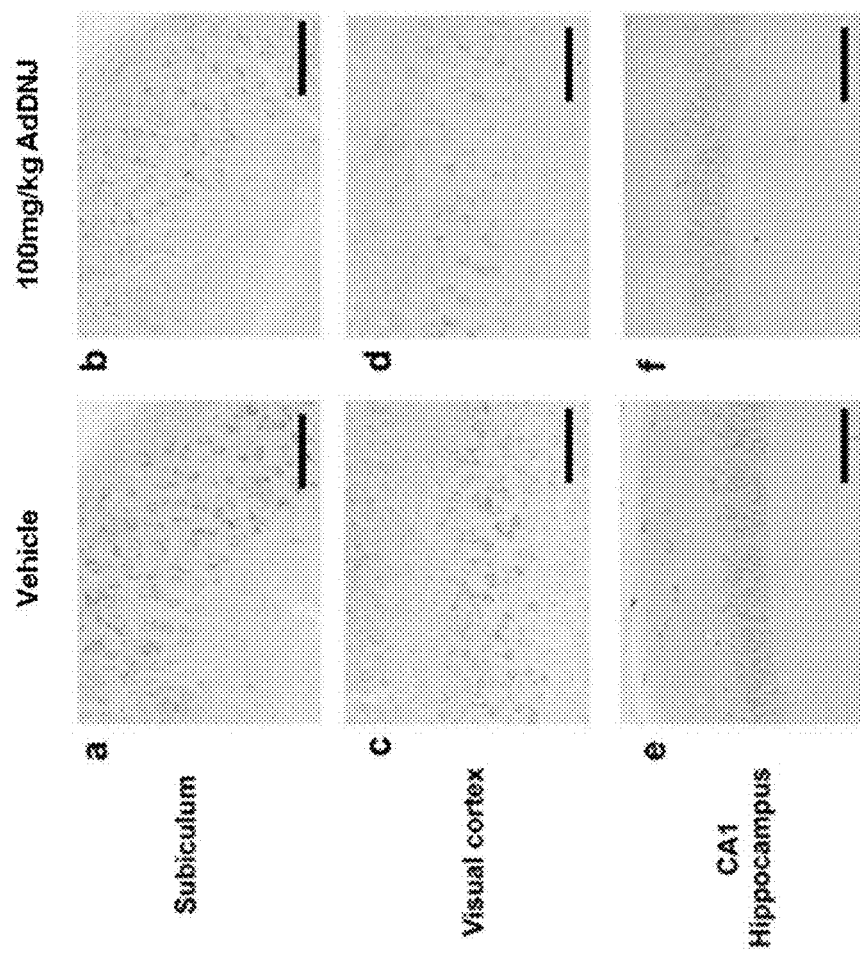
FIGS. 8 a-f

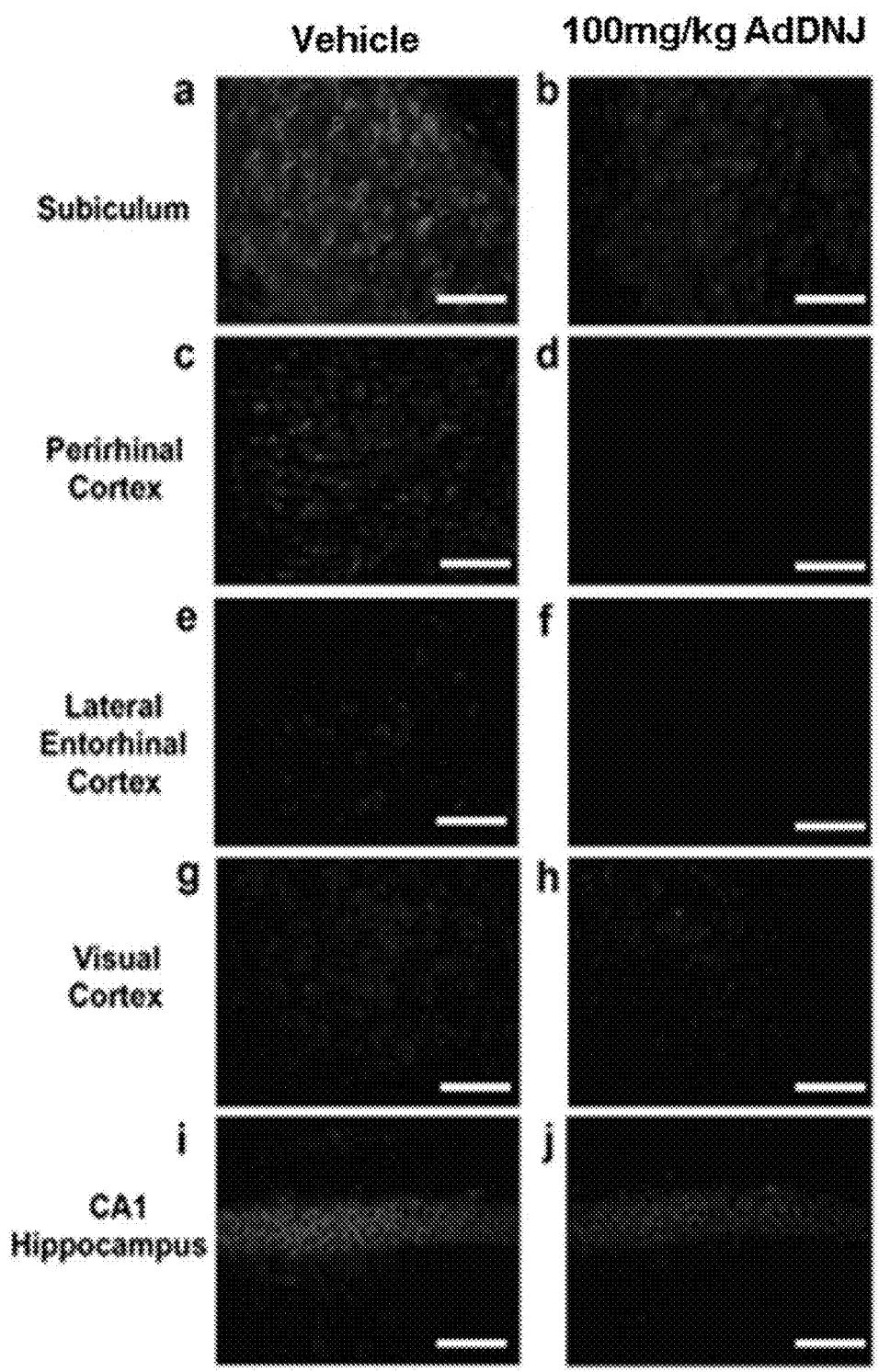
FIGS. 9 a-j

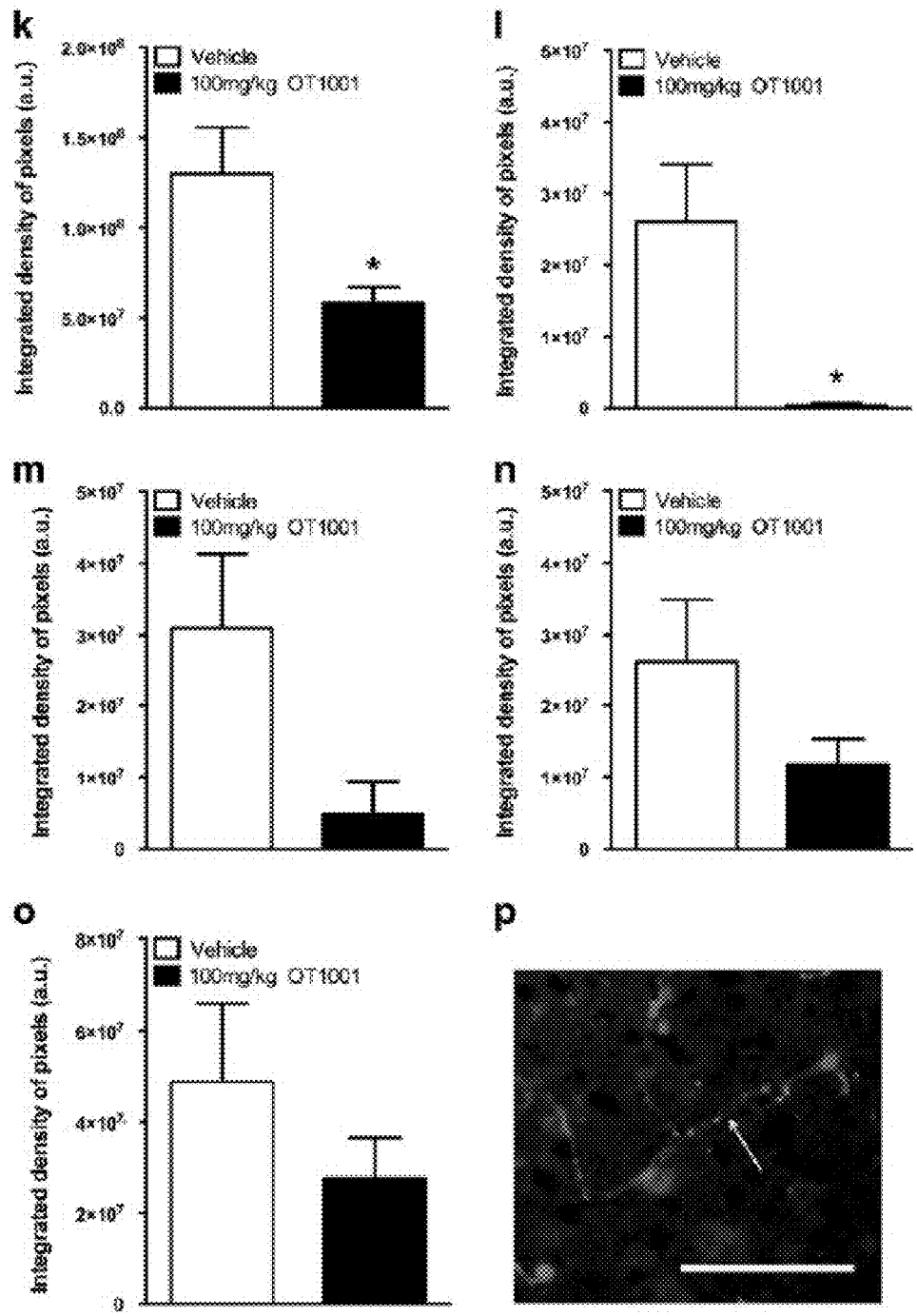
FIGS. 9 k-p

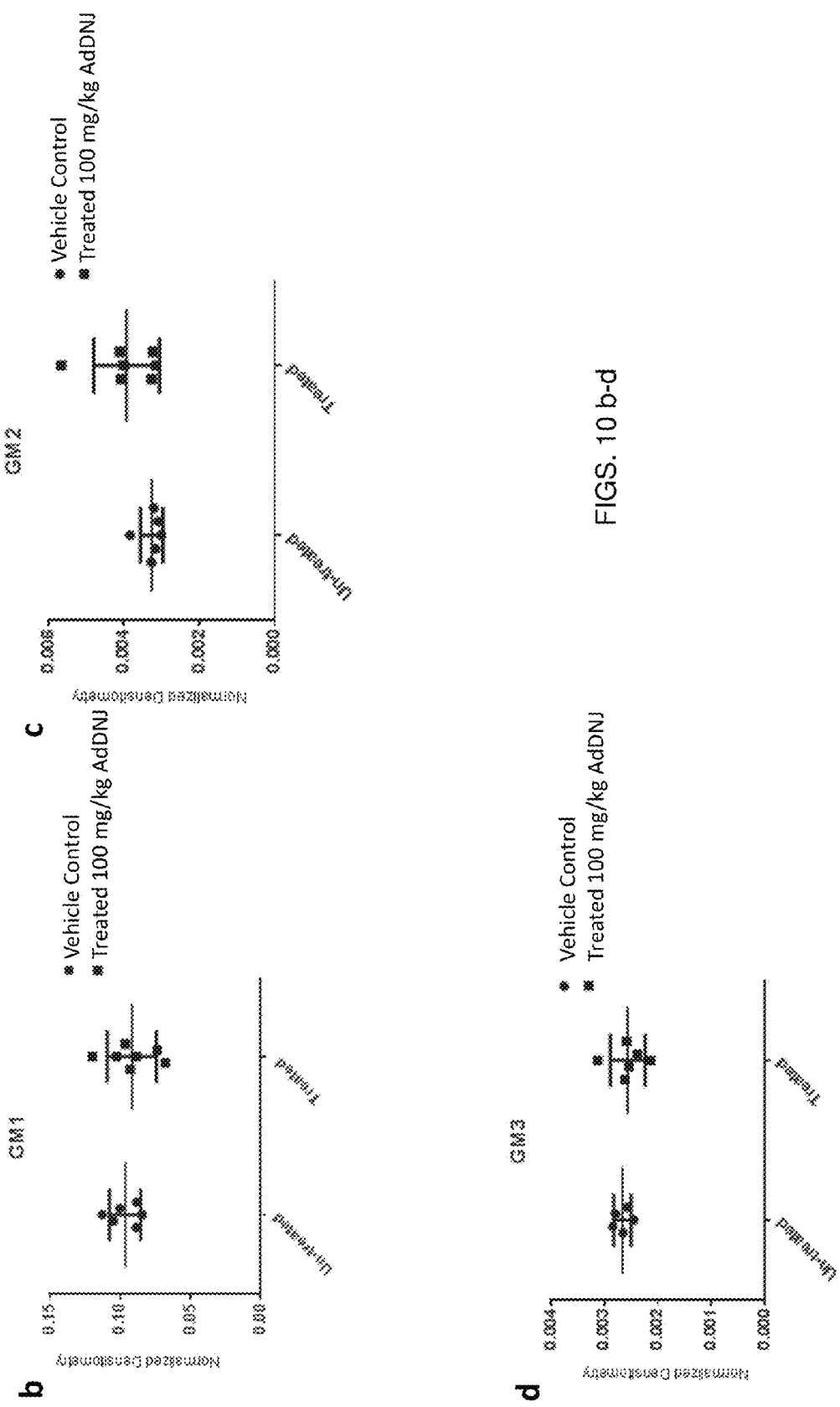
FIGS. 10 b-d

DOSING REGIMENS FOR TREATING AND/OR PREVENTING CEREBRAL AMYLOIDOSES

CROSS-REFERENCE TO RELATED APPLICATIONS

This application claims the benefit under 35 U.S.C. §119(e) to U.S. Provisional Application No. 61/979,408, filed Apr. 14, 2014, the entire contents of which are incorporated herein by reference in their entirety.

TECHNICAL FIELD

The present invention generally pertains to the treatment of human cerebral amyloidoses such as Alzheimer's disease and/or cerebral amyloid angiopathy.

BACKGROUND

Alzheimer's disease is one of the largest socioeconomic healthcare burdens. Alzheimer's disease is characterized by progressive dementia and histopathologically by the presence of neurofibrillary tangles (NFTs) and neuritic (senile) plaques. Plaques consist of a protein called amyloid-beta (Aβ) and tangles are made up of a protein called tau.

Amyloid plaques and NFTs are both hallmarks of Alzheimer's disease (AD). Mutations in amyloid precursor protein (APP) and presenilin lead to early onset forms of Alzheimer's disease, supporting the hypothesis that the processing of APP may also play an important role in the pathogenesis of sporadic AD. Furthermore, the "amyloid hypothesis" predicts that the accumulation of Aβ in some toxic form is harmful to the brain. APP can be processed by α- and β-secretase pathways. To date, most research efforts to develop AD therapies that retard the progression of the disease are focused on inhibition of γ-secretase and β-secretase and the metabolism of APP to form Aβ peptide or activation of α-secretase processing to increase production of the neuroprotective sAPPα peptide while reducing Aβ production. Developing specific β-secretase inhibitors has been difficult, in part because there appears to be a nonlinear relationship between decrease of β-secretase activity in vivo, and a reduction of Aβ peptides in the brain. A further difficulty is the low brain penetration of most inhibitors, γ-secretase inhibitors have been further plagued with severe GI side effects associated with notch inhibition since γ-secretase processes numerous other substrates in addition to APP, including the notch receptor. Additionally, a deficiency of γ-secretase activity has been shown to cause neurodegeneration and may be associated with autosomal-dominant early-onset Alzheimer's disease caused by mutations in presenilin 1 (a component of the γ-secretase complex that contains the active site of the γ-secretase complex).

The majority of efforts aimed at treating Alzheimer's disease have focused on reducing the symptoms of AD. In particular, identification of a lower concentration of choline acetyltransferase in affected neurons of the forebrains of AD patients has led to treatments aimed at inhibiting the hydrolysis of acetylcholine in the synaptic cleft and prolonging the level of acetylcholine at the synapse. Although this strategy has resulted in at least a partial correction of neurotransmitter levels, the therapeutic benefits have been small.

Further, AD is categorized as a tauopathy. Tauopathies are caused by abnormal hyperphosphorylation of tau promoting its aggregation and formation of NFTs. Since mutations in tau and APP both cause dementia, one or both may contribute to the disease progression of AD. It is well understood that mutations leading to altered processing of APP cause AD. Currently, there are no approved therapies for slowing the progression of Alzheimer's disease. Thus, there remains a need for more beneficial AD treatments. While most therapies in development are focused on altering APP metabolism (e.g. β-secretase and γ-secretase inhibition) or blocking tau aggregation, the present invention provides a treatment using pharmacological chaperones which bind to one or more gangliosidases and/or sialidases and thereby increase the production of sAPPα and reduce the production of Aβ and hyperphosphorylated tau.

Similarly, cerebral amyloid angiopathy (CAA) is a disorder characterized by amyloid deposition in the walls of blood vessels of the central nervous system, particularly in the leptomeningeal and cortical arteries. CAA occurs mostly as a sporadic condition in the elderly, and its incidence is associated with advancing age. These sporadic CAA cases are due to deposition of Aβ, originating from proteolytic cleavage of APP. Hereditary forms of CAA are generally familial, more severe and earlier in onset than sporadic CAA. CAA has also recently been recognized as a potential contributor to the development of AD.

All citations herein are incorporated by reference in their entirety.

SUMMARY

It has been found that pharmacological chaperones that target β-hexosaminidase (β-hex) can have many benefits relating to the treatment and/or prevention of cerebral amyloidoses. In particular, the pharmacological chaperone 2-acetamido-1,2-dideoxynojirimycin (AdDNJ) has been found to reduce GAβ pathology in Dutch APP$^{E693Q}$ transgenic mice and corrects the behavioral phenotype of those mice in a dose dependent manner. AdDNJ has good pharmaceutical qualities including good oral bioavailability, brain penetration, tolerability, selectivity and low cytotoxicity. Thus, AdDNJ and other strategies for increasing β-hex activity are expected to help management of human cerebral amyloidosis, such as Alzheimer's disease (AD) and/or cerebral amyloid angiopathy (CAA).

Accordingly, one aspect of the present invention pertains to a method for preventing and/or treating Alzheimer's disease and/or cerebral amyloid angiopathy in a patient at risk for developing or diagnosed with the same by administering an effective amount of 2-acetamido-1,2-dideoxynojirimycin (AdDNJ). In one or more embodiments of this aspect, the method comprises administering to the patient an effective amount of AdDNJ for a first enzyme enhancement period; not administering the AdDNJ for a substrate turnover period; and then administering to the patient an effective amount of AdDNJ for a second enzyme enhancement period.

The first enzyme enhancement period and the second enzyme enhancement period may have the same duration, or they may have different durations. In various embodiments, one or more of the first enzyme enhancement period and the second enzyme enhancement period is a period of about 1 day to about 8 days, such as period of about 4 days to about 6 days. The AdDNJ may be administered daily during one or more of the first enzyme enhancement period and the second enzyme enhancement period.

In one or more embodiments, the AdDNJ is administered orally. Other administration routes include, but are not limited to, intranasal administration.

According to one or more embodiments, the AdDNJ is administered at a dose in the range of about 3 mg/kg/day to about 300 mg/kg/day, such as about 100 mg/kg/day.

In one or more embodiments, not administering the AdDNJ for the substrate turnover period comprises not administering AdDNJ for a period of about 48 hours to about 96 hours, such as a period of about 72 hours. Other exemplary substrate turnover periods include not administering the AdDNJ for about 24 hours or not administering the AdDNJ for about 48 hours.

Various combinations of enzyme enhancement periods and substrate turnover periods are possible. In one exemplary schedule, the first enzyme enhancement period is about 5 days and not administering the AdDNJ for the substrate turnover period comprises not administering AdDNJ for a period of about 72 hours.

Another exemplary schedule includes administering to the patient an effective amount of AdDNJ on a first day; not administering the AdDNJ on a second day; administering to the patient an effective amount of AdDNJ on a third day; not administering the AdDNJ on a fourth day; administering to the patient an effective amount of AdDNJ on a fifth day; and then not administering the AdDNJ for a period of about 72 hours.

In yet another exemplary schedule includes 1, the first enzyme enhancement period is about 3 days and not administering the AdDNJ for the substrate turnover period comprises not administering AdDNJ for a period of about 120 hours.

The method may comprise additional substrate turnover periods and/or additional enzyme enhancement periods. In one or more embodiments, the method comprises alternating between enzyme enhancement periods and substrate turnover periods for a certain total treatment time, such as a treatment time of at least 1 month. The total treatment time may be any suitable period of time for therapy, such as at least 1, 2, 3, 4, 5, 6, 7, 8, 9, 10, 11 or 12 months or 1, 2, 3 or 4 years. In various embodiments, the AdDNJ is administered for an indefinite period of time. Each enzyme enhancement period or each substrate turnover period may be the same as or different from another enzyme enhancement period or substrate turnover period, respectively.

Another aspect of the present invention comprises a kit for treating and/or preventing Alzheimer's disease and/or CAA. In one or more embodiments, the kit comprises one or more dosage forms comprising an effective amount of AdDNJ and instructions for administering the dosage form according to any of the methods described herein. For example, the kit may comprise instructions for administering the dosage forms for a first enzyme enhancement period; not administering the dosage forms for a substrate turnover period; and then administering the dosage forms for a second enzyme enhancement period.

The kit may comprise one or one or more inactive dosage forms that do not comprise an effective amount of AdDNJ. The kit may include instructions for administering the active dosage forms for a first enzyme enhancement period; administering the inactive dosage forms for a substrate turnover period; and then administering the active dosage forms for a second enzyme enhancement period.

The enzyme enhancement period(s) and substrate reduction period(s) may have any of the characteristics described herein.

BRIEF DESCRIPTION OF THE DRAWINGS

FIGS. 1 $a$-$g$ show a summary of potency, selectivity and cell-toxicity summary of the β-hex-targeted pharmacological chaperone AdDNJ. AdDNJ is a specific inhibitor of β-hex (a) and does not inhibit O-GlcNAcase (c-d) at 100 μM or the lysosomal enzymes β-glucocerebrosidase (GCase), α-galactosidase (α-Gal), or β-galactosidase (β-Gal) at 10 μM, the highest concentration tested (e). Additionally, AdDNJ had little or no effect on cell viability for human skin fibroblasts (f) and SH-SY5Y (g) treated with concentrations as high as 1 mM AdDNJ for up to 120 hrs. AdDNJ increases β-hex levels 3-Fold in fibroblasts. Treatment of healthy human derived fibroblasts with AdDNJ (95-780 nM) for five days resulted in a dose dependent increase in total wild-type β-hex levels up to 3-fold (b). Data expressed as mean±s.e.m.

FIGS. 2 $a$-$b$ show a single dose AdDNJ pharmacokinetic study in C57BL/J6 mice. 5-wk-old male C57BL/J6 mice were given a single 100 mg/kg dose of the β-hex-targeted pharmacological chaperone AdDNJ. Plasma (a) and brain (b) AdDNJ profiles. A 100 mg/kg of AdDNJ crossed the blood brain barrier and reached levels in the brain that are predicted to be sufficient to bind and increase β-hex levels (>342 nM) and dropped below Ki (253 nM at pH 5) levels for β-hex within 16 h (n=5 mice per time point). Data expressed as mean±s.e.m.

FIGS. 3 $a$-$b$ show an AdDNJ repeat dose and dose-response study in C57BL/J6 mice. 5-wk-old male C57BL/6 mice were orally gavaged either with vehicle, 30, 100 or 300 mg/kg of the β-hex-targeted pharmacological chaperone AdDNJ daily up to 14 days. Whole brain Hex A&S (a) and Hex B (b) activity (n=5 mice per time point). Data expressed as mean±s.e.m.

FIGS. 5 $a$-$b$ show reduced anxiety and prevention of onset of learning behavior deficits following treatment of AdDNJ in Dutch APP$^{E693Q}$ transgenic mice. 3-mo-old male Dutch APP$^{E693Q}$ transgenic mice were either untreated (n=15), or orally dosed with vehicle (n=15) or AdDNJ (3, 10, 30 or 100 mg/kg AdDNJ; n=13/treatment group) for three months. 6-mo-old vehicle treated Dutch APP$^{E693Q}$ transgenic mice show increased anxiety than 3-mo-old untreated mice in the elevated plus maze, which is reversed following treatment with AdDNJ at all doses tested (a). 3-mo-old untreated mice display intact memory, exploring the novel (new) object more than the familiar (old) object, whereas 6-mo-old vehicle treated Dutch transgenic mice show a learning behavior deficit in novel object recognition (NOR) AdDNJ prevents onset of learning deficit in the NOR test in a dose-dependent manner (b). Data expressed as mean±s.e.m. *P<0.05, ***P<0.001.

FIGS. 7 $a$-$o$ show Aβ and oligomer levels following 3-months treatment of AdDNJ in Dutch APP$^{E693Q}$ transgenic mice. 3-mo-old male Dutch APP$^{E693Q}$ transgenic mice were either untreated, or orally dosed with vehicle or AdDNJ (3, 10, 30 or 100 mg/kg AdDNJ; treated n=13/group) for three months. AdDNJ had no effect on Aβ40 (a-d), Aβ42 (e-h), Aβ42/40 ratio (i-1) or A11 prefibrilar Aβ (m) or oligomers using the antibodies (OC or Nu-4, n-o) (n=5/group). Data expressed as mean±s.e.m.

FIGS. 8 a-f show Aβ immunoreactivity was reduced following treatment of AdDNJ in Dutch APPE693Q transgenic mice. Sagittal brains sections from male Dutch APP$^{E693Q}$ transgenic mice orally dosed either vehicle (a,c,e) or 100 mg/kg AdDNJ (b,d,f) for three months were stained with the antibody 6E10 (vehicle; n=4, 100 mg/kg AdDNJ; n=4). Aβ immunoreactivity was less intense in the subiculum (a,b) but not visual cortex (c,d) nor in CA1 region of the hippocampus (e,f) of AdDNJ treated Dutch APP$^{E693Q}$ transgenic mice. Scale bar a-f 200 μM; and FIGS. 9 a-p show ganglioside-bound Aβ (GAβ) immunoreactivity reduced following treatment of AdDNJ in Dutch APP$^{E693Q}$ transgenic mice. Sagittal brains sections from male Dutch APP$^{E693Q}$ transgenic mice dosed either vehicle (a,c,e,g,i) or AdDNJ (b,d,f,h,j) for three months were staining with GAP (43696C) (vehicle; n=4, 100 mg/kg AdDNJ; n=4). GAP immunoreactivity as detected by 43696C antibody was reduced in the subiculum and perirhinal cortex (k,i). GAP was unchanged in the visual cortex, lateral entorhinal cortex and CA1 region of the hippocampus (m,n,o). Scale bar a-j 200 μM. GAP staining in vessels was detectable in cortical regions (p). Data expressed as mean±s.e.m. *P<0.05.

DETAILED DESCRIPTION

Figure 4C:
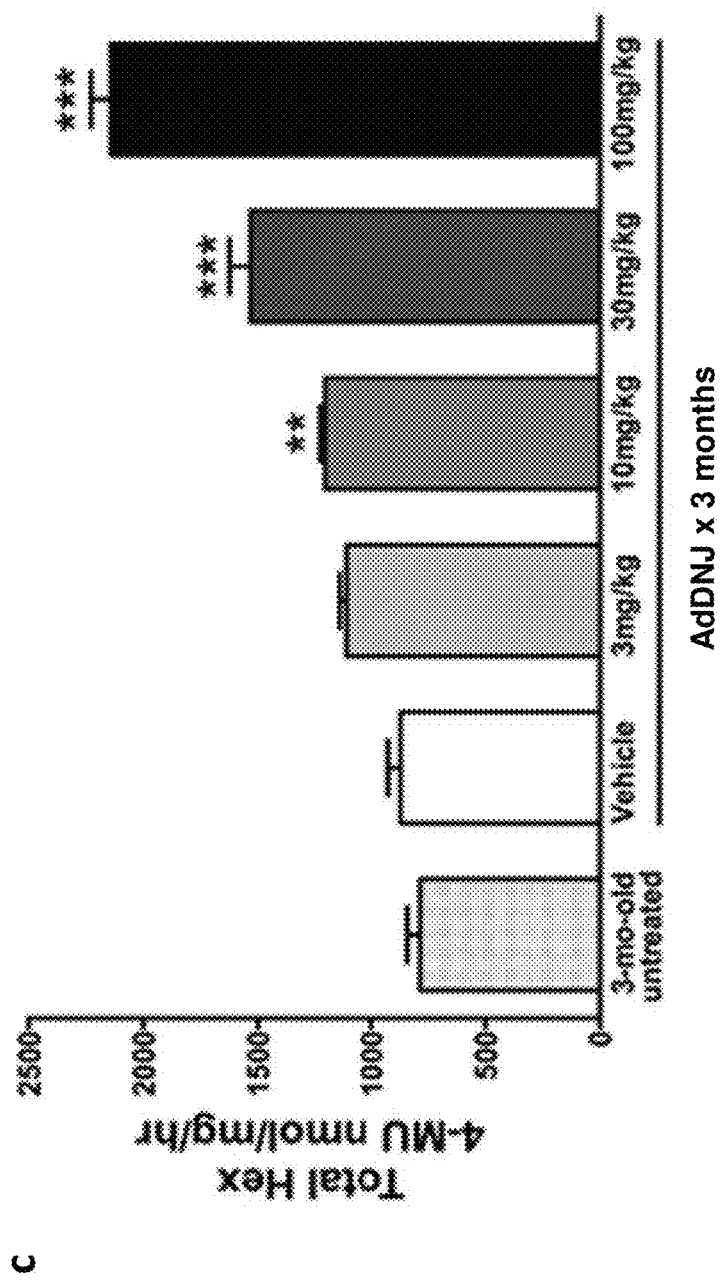
FIGS. 4 $a$-$c$ show increased brain β-hex levels following treatment of AdDNJ in Dutch APP$^{E693Q}$ transgenic mice. 3-mo-old male Dutch APP$^{E693Q}$ transgenic mice were either untreated, or orally dosed with vehicle or AdDNJ for three months. Treatment of AdDNJ increases β-hex B (a), β-hex A&S (b) and total β-hex levels in a dose-dependent manner (untreated; n=3, vehicle; n=6, 3 and 10 mg/kg AdDNJ; n=7, 30 and 100 mg/kg AdDNJ; n=6). Data expressed as mean±s.e.m. One-way ANOVA with Bonferroni posthoc analyses, *P<0.05, P<0.01, *P<0.001.

Aβ is a hydrophobic 38- to 43-amino acid peptide, found in all biological fluids, and derived from the enzymatic cleavage of a larger type I membrane protein, the amyloid precursor protein (APP). Linkage studies of familial AD patients identified a number of mutations in two genes, APP and presenilin, associated with aberrant metabolism of APP and an increased production of aggregating forms of Aβ. It is thought that Aβ forms toxic oligomers which may play a significant role in the pathology of Alzheimer's disease (Shankar et al., 2008).

Gangliosides promote the generation of neurotoxic forms of Aβ in the brain (i.e. oligomers). Gangliosides are sialic acid-containing glycosphingolipids that are found in the outer leaflet of cell membranes, and are particularly abundant on the cell surface of neurons. Gangliosides are known to exist in clusters and to form microdomains on the surface of the plasma membrane. This specific localization of gangliosides enables them to interact with a variety of bioeffectors, including glycoproteins, peptide hormones, and growth factors. Furthermore, gangliosides (e.g. GM1 ganglioside) can promote cell differentiation, prevent loss of neurogenesis, and play a neuroprotective role in in vitro and in vivo models of neuronal injury.

Gangliosides are most abundant in the nervous system and are involved in a variety of functions, including mediation of signal transduction, cell adhesion and cell differentiation. While over 200 gangliosides have been identified, the majority of gangliosides in neurons are catabolized by one or more gangliosidases and/or sialidases.

The products of α-secretase activity, soluble APPα (sAPPα), and β-secretase activity, soluble APPβ (βAPPβ), differ by the inclusion in sAPPα of the first 16 residues of Aβ. Since cleavage of APP by α-secretase bisects the Aβ domain, none of the products of the reaction can give rise to amyloid. Thus, activation of or upregulation of α-secretase activity is hypothesized to prevent or reduce the formation of toxic Aβ oligomers and amyloid plaques, while increasing the shedding of neurotrophic and neuroprotective sAPPα. Interestingly, inhibiting the synthesis of glycosphingolipids and gangliosides has been shown to activate the shedding of sAPPα (Sawamura et al., 2004).

Mutations in APP also cause familial Alzheimer's disease and/or cerebral amyloid angiopathy (CAA). The gangliosides GM2, GM3 and GD3 may modulate regional Aβ deposition since they are expressed in an area-specific manner in the brain (Yamamoto et al., 2006). Assembly of hereditary variant Dutch- and Italian-type Aββ, and Flemish-type Aβ was accelerated by GM3 ganglioside and GD3 ganglioside, respectively. Notably, cerebrovascular smooth muscle cells, which compose the cerebral vessel wall where the Dutch- and Italian-type Aββ deposit, exclusively express GM2 and GM3 (Yamamoto et al., 2006). Thus, the assembly of hereditary Aβ variants may be accelerated by local environmental factors, such as the presence of particular gangliosides in the brain.

Glycosphingolipids and gangliosides have recently been implicated in misfolding and aggregation of neurodegeneration-related proteins (e.g., genetic linkage of Parkinson's disease to glucocerebrosidase mutations) (Alcalay et al., 2012; Daniele et al., 2012). Growing evidence indicates that abnormalities in ganglioside metabolism may contribute to Alzheimer's disease (AD) pathogenesis and cerebral amyloid angiopathy (CAA) by accelerating the generation of neurotoxic forms of Aβ in the brain and vasculature. During aging and neurodegeneration, the physiochemical properties of membranes change, resulting in imbalances in the proportion of lipids in membranes and/or altered ratios of membrane lipids, which may contribute to the pathogenesis of AD (Yanagisawa, 2007; Mutoh et al., 2006; Hayashi et al., 2004; Karcun et al., 1991; Brooksbank et al., 1989. Matsuzaki, 2007). Consistent with this idea, elevated monosialoganglioside (GM1, GM2 and GM3) levels have been reported in the cortex of AD brains (Gylys et al., 2007), where they apparently localize to membrane microdomains (detergent resistant membranes) in the frontal, temporal and parietal cortices of affected brains (Kracun et al., 1991; Molander-Melin et al., 2005). Also, ganglioside-bound Aβ (GAβ) peptide has been detected in brains exhibiting only the very earliest stages of AD pathology (Yanagisawa et al., 1995; Yanagisawa et al., 1997; Yanagisawa et al., 1998), suggesting that gangliosides may play some role(s) early in the pathogenesis of AD, such as the seeding of Aβ fibrils (Yanagisawa et al., 2007; Yamamoto et al., 2005; Selkoe, 1995). Of note, some mutant forms of Aβ (especially those mutations that favor oligomerization) show a particular susceptibility to the pro-aggregation properties of GM2 and GM3 (Yamamoto et al., 2005; Yamamoto et al., 2006).

β-Hexosaminidase (β-Hex) catabolizes GM2 gangliosides and its deficiency causes the autosomal recessive lysosomal storage disorders Tay-Sachs disease and Sandhoff disease (Mahuran, 1999). Intraneuronal accumulation of anti-Aβ-like immunoreactivity has been found using antibody 4G8, anti-α-synuclein-like immunoreactivity, and antipTau-like immunoreactivity in the brains of HEXB KO mice (Keilani et al., 2012). Biochemical and immunohistochemical analysis confirmed that the intraneuronal 4G8 immunoreactivity represents APP-CTFs and/or Aβ but not full-length APP. In addition, increased levels of Aβ40 and Aβ42 peptides were found in the lipid-associated fraction (as compared to that recovered from wildtype brains). Accumulation of ganglioside-bound Aβ immunoreactivity was also observed in the brains of HEXB KO mice and in the brains of human subjects with GM1 and GM2 gangliosidoses. Taken together, these results draw a link between the accumulation of gangliosides and the accumulation of Aβ.

GM2 and GM3 gangliosides have been shown to promote assembly in vitro of the Dutch-, Iowa- and Italian-type mutant Aβ peptides that are especially prone to oligomerization (Yamamoto et al., 2005; Yamamoto et al., 2006). It has been shown that the generation and characterization of Dutch APPE693Q transgenic mice that accumulate Aβ oligomers in the brain (specifically within neurons in the subiculum, visual cortex and CA1 region of the hippocampus) and develop anxiety and learning behavior deficits, but they never develop amyloid plaques (Gandy et al., 2010). It was hypothesized that increasing β-hex activity using a β-hex-targeted "pharmacological chaperone" to reduce GM2 levels will reduce Aβ oligomerization and prevent behavioral changes in Dutch APPE693Q transgenic mice. Pharmacological chaperones represent novel treatment strategies in their actions as small molecules that selectively bind and stabilize target proteins to facilitate proper folding and to reduce premature degradation (Tropak et al., 2007; Maegawa et al., 2007; Tropak et al., 2004; Rountree et al, 2009). These pharmacological chaperones are small molecules that bind proteins reversibly, thereby stabilizing the protein target and increasing its half-life. Pharmacological chaperone therapies for cystic fibrosis and several lysosomal storage disorders, including Fabry, Gaucher, Pompe, Sandhoff and Tay-Sachs diseases, have been, or continue to be, assessed in clinical trials (Boyd et al, 2013; Wustman et al, 2012; Osher et al., 2011; Clarke, et al., 2011).

One aspect of the present invention provides dosing regimens for the treatment and/or prevention of cerebral amyloidoses such as Alzheimer's disease and/or cerebral amyloid angiopathy using pharmacological chaperones targeted to β-Hex. In one or more embodiments of this aspect, the pharmacological chaperone is 2-acetamido-1,2-dideoxynojirimycin (AdDNJ).

AdDNJ, also known as 2-acetamido-1,2,5-trideoxy-1,5-imino-D-glucitol, is a compound having the following structure:

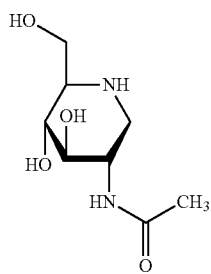

AdDNJ may be administered in the free form as shown above, or may be administered in the form of a pharmaceutically acceptable salt, solvate, or prodrug thereof.

In one or more embodiments, the AdDNJ is administered in a unique dosing regimen that balances the chaperoning and inhibitory effects of AdDNJ. For example, the AdDNJ may be administered for an enzyme enhancement period in which the AdDNJ enhances β-hex activity by facilitating proper folding, trafficking, non-aggregation, etc. After the enzyme enhancement period, the AdDNJ may be not administered for a substrate turnover period to allow the AdDNJ concentration to drop below inhibitory concentrations to enable the disassociation of the AdDNJ from the β-hex. The dosing regimen may include a second enzyme enhancement period, which may be the same as or different from the first enzyme enhancement period. The dosing regimen may include a second substrate turnover period, which may be the same or different from the first substrate turnover period. The dosing regimen may also include cycling between enzyme enhancement periods and substrate turnover periods.

Exemplary enzyme enhancement periods may be in the range of a few hours to several days. For example, the AdDNJ may be administered once a day or multiple times a day (2×, 3×, 4×, etc.) for a period of one day to ten days. In various embodiments, the enzyme enhancement period is about 1, 2, 3, 4, 5, 6, 8, 10, 12, 24, 36, 48, 60, 72, 96, 120 hours or about 1, 2, 3, 4, 5, 6, 7, 8, 9 or 10 days.

Exemplary substrate turnover periods may also be in the range of a few hours to several days. The substrate turnover period is defined as the time between successive enzyme enhancement periods. In various embodiments, the enzyme enhancement period is about 1, 2, 3, 4, 5, 6, 8, 10, 12, 24, 36, 48, 60, 72, 96, 120 hours or about 1, 2, 3, 4, 5, 6, 7, 8, 9 or 10 days. For example, if the substrate turnover period is about 24 hours and the enzyme enhancement period consists of a single administration of AdDNJ, then the time between successive AdDNJ administrations is about 24 hours (i.e. once a day). Similarly, if the substrate turnover period is about 48 hours and the enzyme enhancement period consists of a single administration of AdDNJ, then the time between successive AdDNJ administrations is about 48 hours (i.e. every other day). Further examples include substrate turnover periods of about 72 hours (e.g. administration on Monday and Thursday but not Tuesday and Wednesday). The terms "about 24 hours", "about 48 hours" and "about 72 hours" do not require that the administrations be at the same time each administration day, but merely represent that the administrations occur on different days.

Examples of suitable dosing regimens include, but are not limited to, the following administrations:
  a. once, twice or three times a day for five consecutive days a week (e.g. Monday-Friday);
  b. once, twice or three times a day for seven days a week (e.g. Monday-Sunday);
  c. once, twice or three times a day for three consecutive days a week (e.g. Monday-Wednesday);
  d. once, twice or three times a day for three non-consecutive days a week (e.g. Monday, Wednesday, Friday); and
  e. once, twice or three times a day, every other day.

Each individual administration may include a therapeutically effective amount of AdDNJ or a salt, solvate or prodrug thereof. Each administration may include an amount of AdDNJ or a salt, solvate or prodrug thereof in the range from about 1 mg/kg to about 1,000 mg/kg. Exemplary amounts include 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg and 1,000 mg/kg. Exemplary amounts also include 25 mg, 50 mg, 75 mg, 100 mg, 125 mg, 150 mg, 175 mg, 200 mg, 250 mg, 300 mg, 400 mg, 500 mg, 600 mg, 700 mg, 800 mg, 900 mg, 1,000 mg, 1,100 mg, 1,200 mg, 1,300 mg, 1,400 mg, 1,500 mg, 1,600 mg, 1,700 mg, 1,800 mg, 1,900 mg, 2,000 mg, 2,500 mg, 3,000 mg, 3,500 mg, 4,000 mg, 4,500 mg, 5 g, 6 g, 7 g, 8 g, 9 g, 10 g, 11 g, 12 g, 13 g, 14 g, 15 g, 16 g, 17 g, 18 g, 19 g and 20 g. The amount administered during different administrations may be the same or the administered amount may vary.

Another aspect of present invention provides kits for the treatment and/or prevention of cerebral amyloidoses such as Alzheimer's disease and/or CAA using pharmacological chaperones targeted to β-Hex. In one or more embodiments of this aspect, the pharmacological chaperone is 2-acetamido-1,2-dideoxynojirimycin (AdDNJ). The kit includes one or more dosage forms comprising an effective amount of the pharmacological chaperone. The kit may include instructions for administering the pharmacological chaperone according to any of the dosing regimens described herein. The kit may also include inactive dosage forms that do not include the pharmacological chaperone. Either the active and/or inactive dosage forms may include other therapeutic agents such as those suitable for combination therapy.

The pharmacological chaperone can be formulated to be suitable for any route of administration, including e.g., orally in the form of tablets or capsules or liquid, or in sterile aqueous solution for injection. When the pharmacological chaperone is formulated for oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); or preservatives (e.g., methyl or propyl-p-hydroxybenzoates or sorbic acid). The liquid preparations may also contain buffer salts, flavoring, coloring or sweetening agents as appropriate. Preparations for oral administration may be suitably formulated to give controlled or sustained release of the compound.

In one or more embodiments of the present invention, the compound is administered in a dosage form that permits systemic distribution or uptake, such that the compound may cross the blood-brain barrier so as to exert effects on neuronal cells. Such dosage forms that permit systemic distribution or uptake may be oral or parenteral. In some embodiments, the compound may be distributed systemically, including crossing the blood-brain barrier. For example, pharmaceutical formulations of the compound suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, polyethylene glycol, and the like), suitable mixtures thereof, or vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate or gelatin.

Sterile injectable solutions are prepared by incorporating the compound in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrolidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a commonly used excipient.

The formulation can also contain a non-ionic detergent. Examples of non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

The therapeutic agent(s) may be administered orally or parenterally, including intravenously, subcutaneously, intraarterially, intraperitoneally, ophthalmically, intramuscularly, buccally, rectally, vaginally, intraorbitally, intracerebrally, intradermally, intracranially, intraspinally, intraventricularly, intrathecally, intracisternally, intracapsularly, intrapulmonarily, intranasally, transmucosally, transdermally, or via inhalation. In one preferred embodiment, the therapeutic agent(s) is administered orally.

Administration of therapeutic agent(s) may be by periodic injections of a bolus of the formulation, or may be administered by intravenous or intraperitoneal administration from a reservoir which is external (e.g., an i.v. bag) or internal (e.g., a bioerodable implant). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780, 014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can be administered using these methods.

Subcutaneous injections have the advantages allowing self-administration, while also resulting in a prolonged plasma half-life as compared to intravenous administration. Furthermore, a variety of devices designed for patient convenience, such as refillable injection pens and needle-less injection devices, may be used with the formulations of the present invention as discussed herein.

A suitable pharmaceutical preparation is in a unit dosage form. In such form, the preparation is subdivided into suitably sized unit doses containing appropriate quantities of the active component, e.g., an effective amount to achieve the desired purpose. In certain embodiments, the therapeutic agent(s) is administered in one or more daily doses (e.g., once-a-day, twice-a-day, thrice-a-day). In certain embodiments, the therapeutic agent(s) is administered in intermittently.

According to one or more embodiments of the present invention, individuals to be treated may have or be at risk of developing any cerebral amyloidosis. Such cerebral amyloidoses include, but are not limited to, Alzheimer's disease and cerebral amyloid angiopathy (CAA). For example, the cerebral amyloidosis can be any form of Alzheimer's disease, including early onset familial Alzheimer's disease. The cerebral amyloidosis can also be any form of CAA, including hereditary forms of CAA and CAA with Alzheimer's disease. The individual may have a risk factor for a cerebral amyloidosis or be at risk for developing a cerebral amyloidosis. Such risk factors include, but are not limited to, the ApoE4 allele of Apolipoprotein E, which is associated with an increased risk for developing Alzheimer's disease and CAA. The individual may have already been diagnosed with a cerebral amyloidosis. Further, the individual may not have been diagnosed with a cerebral amyloidosis, but displays hallmarks of one of the diseases. In a further embodiment, Alzheimer's disease is caused by or linked to Down syndrome.

Further, the treatment may include combinations of one or more pharmacological chaperones and may also be combined with other known Alzheimer treatments or other cerebral amyloidoses. Treatment may also include combinations of one, two, three or more pharmacological chaperones or a combination of one, two, three or more chaperones with one or more inhibitors of glucosylceramide synthase. Combination therapies including one or more chaperones with one or more inhibitors of glucosylceramide synthase and may increase gangliosidase activity and decrease glucosylceramide synthase activity.

DEFINITIONS

The terms used in this specification generally have their ordinary meanings in the art, within the context of this invention and in the specific context where each term is used. Certain terms are discussed below, or elsewhere in the specification, to provide additional guidance to the practitioner in describing the invention and how to make and use the invention.

As used herein, the term "pharmacological chaperone", refers to a molecule that specifically binds to one or more gangliosidases and/or sialidases, or glucocerebrosidase, and has one or more of the following effects: (i) enhancing the formation of a stable molecular conformation of the protein; (ii) enhances proper trafficking of the protein from the ER to another cellular location, preferably a native cellular location, i.e., preventing ER-associated degradation of the protein; (iii) preventing aggregation of conformationally unstable, i.e., misfolded proteins; (iv) restoring or enhancing at least partial wild-type function, stability, and/or activity of the protein; and/or (v) improving the phenotype or function of the cell. Thus, a pharmacological chaperone for gangliosidases or sialidases is a molecule that binds to one or more gangliosidases and/or sialidases, resulting in proper folding, trafficking, non-aggregation, and increased activity of the gangliosidase and/or sialidase. It includes specific binding molecules, e.g., active site-specific chaperones, inhibitors, allosteric binders, non-active site binders that enhance protein stability. In one or more embodiments, the pharmacological chaperone is specific to β-Hex, such as AdDNJ.

The term "pharmacological chaperones" (PCs) refers to small molecules that selectively bind and stabilize target proteins to facilitate proper folding, reduce premature degradation and increase the efficiency of ER export. The small molecules are called "chaperones" because they help the proteins get from the where they are synthesized (the ER) to their intended location (e.g., the lysosome or the cell surface). The molecules are reversible binders which bind and stabilize the protein target, help restore proper trafficking, and then dissociate so the protein can carry out its proper function. The "pharmacological" modifier denotes molecular specificity: the molecules are designed to interact with and stabilize only a single intended protein target, and PCs do not generally affect multiple proteins or cellular processes such as protein trafficking, ER quality control, proteasome function, or the activity of biological chaperones (such as the heat shock proteins). This approach is broadly applicable to diseases where increasing the function of a specific protein (mutant or wild-type) is predicted to provide therapeutic benefit.

The retention and premature degradation of incorrectly folded proteins is not restricted to mutant proteins. It has been shown that a large fraction (up to 30%) of all newly synthesized proteins is targeted for premature degradation by the proteasomes. Subsequent studies have shown that pharmacological chaperones can increase cellular levels for many wild-type proteins by promoting protein folding, stability and ER export.

Molecular Chaperones Stabilize Protein Conformation.

In the human body, proteins are involved in almost every aspect of cellular function. Certain human diseases result from mutations that cause changes in the amino acid sequence of a protein which reduce its stability and may prevent it from folding properly. The majority of genetic mutations that lead to the production of less stable or misfolded proteins are called missense mutations. These mutations result in the substitution of a single amino acid for another in the protein. Because of this error, missense mutations often result in proteins that have a reduced level of biological activity. In addition to missense mutations, there are also other types of mutations that can result in proteins with reduced biological activity.

Proteins generally fold in a specific region of the cell known as the endoplasmic reticulum, or ER. The cell has quality control mechanisms that ensure that proteins are folded into their correct three-dimensional shape before they can move from the ER to the appropriate destination in the cell, a process generally referred to as protein trafficking. Misfolded and/or unstable proteins are often eliminated by the quality control mechanisms after initially being retained in the ER. In certain instances, misfolded proteins can accumulate in the ER before being eliminated.

The retention of misfolded proteins in the ER interrupts their proper trafficking, and the resulting reduced biological activity can lead to impaired cellular function and ultimately to disease. In addition, the accumulation of misfolded proteins in the ER may lead to various types of stress on cells, which may also contribute to cellular dysfunction and disease.

Endogenous molecular chaperones are present in virtually all types of cells and in most cellular compartments. Some are involved in the transport of proteins and permit cells to survive under stresses such as heat shock and glucose starvation. Among the endogenous chaperones (molecular chaperones), BiP (immunoglobulin heavy-chain binding protein, Grp78) is the best characterized chaperone of the ER. Like other chaperones, BiP interacts with many secretory and membrane proteins within the ER throughout their maturation. When nascent protein folding proceeds smoothly, this interaction is normally weak and short-lived. Once the native protein conformation is achieved, the molecular chaperone no longer interacts with the protein. BiP binding to a protein that fails to fold, assemble, or be properly glycosylated becomes stable, and usually leads to degradation of the protein through the ER-associated degradation pathway. This process serves as a "quality control" system in the ER, ensuring that only those properly folded and assembled proteins are transported out of the ER for further maturation, and improperly folded proteins, or unstable proteins, are retained for subsequent degradation. Due to the combined actions of the inefficiency of the thermodynamic protein folding process and the ER quality control system, only a fraction of some wild-type proteins become folded into a stable conformation and successfully exit the ER.

Pharmacological Chaperones Derived from Specific Enzyme Inhibitors Rescue Mutant Enzymes and Enhance Wild-Type Enzymes.

The binding of small molecule inhibitors of enzymes associated with lysosomal storage diseases (LSDs), for instance, can increase the stability of both mutant enzyme and the corresponding wild-type enzyme (see U.S. Pat. Nos. 6,274,597; 6,583,158; 6,589,964; 6,599,919; 6,916,829, and 7,141,582 all incorporated herein by reference). In particular, it was discovered that administration of small molecule derivatives of glucose and galactose, which are specific, selective competitive inhibitors for several target lysosomal enzymes, effectively increased the stability of the enzymes in cells in vitro and, thus, increased trafficking of the enzymes to the lysosome. Thus, by increasing the amount of enzyme in the lysosome, hydrolysis of the enzyme substrates is expected to increase. Since the mutant enzyme protein is unstable in the ER, the enzyme protein is retarded in the normal transport pathway (ER→Golgi apparatus→endosomes→lysosome) and prematurely degraded. Therefore, certain compounds which binds to and increases the stability of a mutant enzyme, may serve as "chaperones" for the enzyme and increase the amount that can exit the ER and move to the lysosomes.

Since some enzyme inhibitors are known to bind specifically to the catalytic center of the enzyme (the "active site"), resulting in stabilization of enzyme conformation in vitro, these inhibitors were proposed, somewhat paradoxically, to be effective chaperones that could help restore exit from the ER, trafficking to the lysosomes, hydrolytic activity. These specific pharmacological chaperones were designated "active site-specific chaperones (ASSCs)" or "specific pharmacological chaperones" since they bound in the active site of the enzyme in a specific fashion. Pharmacological chaperone therapy has potential advantages over enzyme replacement therapy (ERT) since a small molecule can be orally administered and may have superior biodistribution compared to protein-based therapies.

In addition to rescuing the mutant enzymes, the pharmacological chaperones enhance ER secretion and activity of wild-type enzymes. Thus, a compound that induces a stable molecular conformation of an enzyme during folding serves as a "chaperone" to stabilize the enzyme in a proper conformation for exit from the ER.

The term "ganglioside" or "sialoganglisides" refers to glycosphingo lipids consisting of N-acylsphingosine and an oligosaccharide chain bearing one or more N-acetyl-neuraminic acid (sialic acid, NeuAc) residues.

The term "asialogangliosides" refers to gangliosides without N-acetylneuraminic acid (sialic acid, NeuAc) residues and include LacCer, GA2 and GA1 (Ariga et al.).

The term "gangliosidase" refers to sialidases and exoglycohydrolases which remove individual N-acetylneuraminic acid (sialic acid, NeuAc) and sugar residues sequentially from the non-reducing terminal unit of gangliosides and asialogangliosides. This degradation occurs mainly through the endocytosis-endosome-lysosome pathway. Examples of gangliosidases included sialidase 2 (neuraminidase 2; NEU2), sialidase 3 (neuraminidase 3; NEU3), sialidase 4 (neuraminidase 4; NEU4), β-galactosidase (GLB1), β-hexosaminidase A (HEXA/HEXB), β-hexosaminidase B (HEXB), and β-hexosaminidase S (HEXS).

The term "sialidases" refers to enzymes that remove individual N-acetylneuraminic acid (sialic acid, NeuAc) residues from the non-reducing terminal unit of gangliosides, oligosaccharides and glycoproteins. The term "sialidases" includes the enzymes sialidase 2 (neuraminidase 2), sialidase 3 (neuraminidase 3) and sialidase 4 (neuraminidase 4), which remove individual N-acetylneuraminic acid residues from gangliosides in the endosome-lysosome pathway, and sialidase 1, which removes individual N-acetylneuraminic acid residues from oligosaccharides and glycoproteins. N-acetylneuraminic acid residues on gangliosides have been shown to increase Aβ binding affinity and increase the tendency to induce β-sheet conformation. It was recently reported that knocking out disialoganglioside synthase (GD3S) in APP/PSEN mice (APPswe+PSEN1 A'E9) prevented both the accumulation of Aβ and the subsequent development of memory deficits that are characteristic of APP/PSEN mice. Bernardo, et ah, Neurobiology of Aging. In Press, Corrected Proof, "Elimination of GD3 synthase improves memory and reduces amyloid-[beta] plaque load in transgenic mice." GD3S links sialic acid to sialic acid through an α-2,8-linkage and is required for the synthesis of b- and c-series gangliosides. These results suggest that decreasing sialic acid content on gangliosides could be beneficial in treating AD.

The lysosomal enzyme "β-Galactosidase" is an exohydrolase that removes β 1,3-galactose from the non-reducing end of asialo- and sialo-gangliosides. Mutations in the gene that encodes β-galactosidase, GLB1, causes the lysosomal storage disorder GM1 gangliosidosis, which results from a deficiency in β-galactosidase activity and the accumulation of GA1 and GM1 gangliosides. Beutler, E. et al., Biol. Chem. 247(22): 7195-200 (1972). GM1 ganglioside is a major component of the microdomains that promote the generation and assembly of Aβ in cell culture, and Aβ bound to GM1 (v̈Aβ) has been found in brains exhibiting early stages of AD pathology.

The lysosomal enzymes β-Hexosaminidase A and B hydrolyze β-linked N-acetylgalactosamine (GalNAc) from the non-reducing end of asialo- and sialo-gangliosides. While GM1 gangliosides have received the most attention, other a-series gangliosides (GD1A, GM2 and GM3) also bind and promote the assembly of Aβ in vitro.

There are two isoenzymes of β-hexosaminidase, HEXA and HEXB. HEXA consists of a α-subunit and β-subunit (αβ), while HEXB consists of two β-subunits (ββ). HEXA encodes the α-subunit of HEXA and HEXB encodes the β-subunit of HEXA and HEXB. Mutations in HEXA causes the lysosomal storage disorder Tay-Sachs disease, which results from a deficiency in HEXA activity and the accumulation of GM2. Mutations in HEXB cause the lysosomal storage disorder Sandhoff disease, which results from a deficiency in HEXA and HEXB activities and the accumulation of GM2 and GA2.

As used herein, the term "specifically binds" refers to the interaction of a pharmacological chaperone with gangliosidases and/or sialidases, or glucocerebrosidase, specifically, an interaction with amino acid residues of a gangliosidases and/or a sialidases, or glucocerebrosidase, that directly participate in contacting the pharmacological chaperone. A pharmacological chaperone specifically binds a target protein, e.g., β-hexosaminidase B, to exert a chaperone effect on the enzyme and not a generic group of related or unrelated proteins. The amino acid residues of β-hexosaminidase that interact with any given pharmacological chaperone may or may not be within the protein's "active site." Specific binding can be evaluated through routine binding assays (e.g. inhibition, thermal stability) or through structural studies, e.g., co-crystallization, NMR, and the like.

As used herein, the terms "enhance stability" or "increase stability" refers to increasing an enzymes resistance to irreversible inactivation in vitro or in a cell contacted with a pharmacological chaperone specific for a gangliosidases and/or sialidases, or for glucocerebrosidase, relative to gangliosidases and/or sialidases (preferably of the same cell-type or the same cell, e.g., at an earlier time), or for glucocerebrosidase, that are not contacted with the pharmacological chaperone. Increasing protein stability increases the half-life of the protein in the ER and the amount of functional protein trafficked from the ER. In one aspect of the invention the stability of a wild type gangliosidase or sialidase, or glucocerebrosidase, is enhanced or increased. In another aspect of the invention the conformational stability of a mutant gangliosidase or sialidase or glucocerebrosidase is enhanced or increased.

As used herein, the terms "enhance trafficking" or "increase trafficking" refer to increasing the efficiency of the transport of a gangliosidase and/or sialidase or glucocerebrosidase to the cytosol (sialidase 2) or the endosomes and lysosomes of a cell contacted with a pharmacological chaperone specific to one or more gangliosidases and/or sialidases or glucocerebrosidase, relative to the efficiency of transport of a gangliosidase and/or a sialidase or glucocerebrosidase in a cell (preferably of the same cell-type or the same cell, e.g., at an earlier time) not contacted with the pharmacological chaperone specific for a gangliosidase and/or a sialidase or glucocerebrosidase.

As used herein, the terms "enhance activity" or "increase activity" refer to increasing the activity of gangliosidases and/or sialidases or glucocerebrosidase, as described herein, in a cell contacted with a pharmacological chaperone specific for one or more gangliosidases and/or sialidases or glucocerebrosidase, relative to the activity of gangliosidases and/or sialidases or glucocerebrosidase in a cell (preferably of the same cell-type or the same cell, e.g., at an earlier time) not contacted with the pharmacological chaperone specific for one or more gangliosidases and/or sialidases or glucocerebrosidase. Pharmacological chaperones of the present invention may also increase enzyme activity by increasing the total amount of enzyme in the cell and/or by increasing an enzyme's specific activity.

The term "specific activity" refers to the amount of substrate an enzyme converts per milligram of protein in an enzyme preparation, per unit of time.

As used herein, the terms "enhance level" or "increase level" refer to increasing the level of one or more gangliosidases and/or sialidases or glucocerebrosidase in a cell contacted with a pharmacological chaperone specific for one or more gangliosidases and/or sialidases or glucocerebrosidase, relative to the level of gangliosidases and/or sialidases or glucocerebrosidase in a cell (preferably of the same cell-type or the same cell, e.g., at an earlier time) not contacted with the pharmacological chaperone specific for one or more gangliosidases and/or sialidases or glucocerebrosidase.

The term "stabilize a proper conformation" refers to the ability of a gangliosidase and/or a sialidase or glucocerebrosidase pharmacological chaperone to induce or stabilize a conformation of a mutated or wild type gangliosidase and/or sialidase or glucocerebrosidase enzyme that is functionally identical to the conformation of the wild-type gangliosidase and/or sialidase or glucocerebrosidase that performs its intended function.

The term "functionally identical" means that while there may be minor variations in the conformation (almost all proteins exhibit some conformational flexibility in their physiological state), conformational flexibility does not result in (1) protein aggregation, (2) elimination through the endoplasmic reticulum-associated degradation pathway, (3) impairment of protein function, e.g., APP metabolic activity, and/or (4) improper transport within the cell, e.g., localization to the cytosol, to a greater or lesser degree than that of the wild-type protein.

The term "stable molecular conformation" refers to a conformation of a protein, i.e., a gangliosidase and/or sialidase or glucocerebrosidase, induced by a pharmacological chaperone that provides at least partial wild-type function in the cell or to enhance wild-type function. For example, a stable molecular conformation of a gangliosidase and/or sialidase or glucocerebrosidase would be one where the gangliosidase and/or sialidase or glucocerebrosidase leaves the ER and traffics to the cytosol, instead of misfolding and being degraded and/or not performing its intended function. In addition, a stable molecular conformation of a mutated gangliosidase and/or sialidase or glucocerebrosidase may also possess full or partial activity. However, it is not necessary that the stable molecular conformation have all of the functional attributes of the wild-type protein.

The term "activity" refers to the normal intended physiological function of a wild-type gangliosidase and/or sialidase or glucocerebrosidase in a cell. For example, gangliosidase and/or sialidase activity includes catabolism of gangliosides and glucocerebrosidase activity includes catabolism of the glycosphingolipid glucosylceramide. Such functionality can be tested by any means known to establish functionality.

The term "ganglioside catabolism" refers to the removal of individual sialic acid and sugar residues sequentially from the non-reducing terminal unit of asialo- and sialo-gangliosides by sialidases and exoglycohydrolases with the formation of ceramide. This degradation occurs mainly through the endocytosis-endosome-lysosome pathway with the exception of sialidase 2, which is located in the cytosol.

In one non-limiting embodiment, a gangliosidase and/or sialidase, or glucocerebrosidase polypeptide may be encoded for by any nucleic acid molecule exhibiting 50%, 60%, 70%>, 80%> and up to 100% homology to the nucleic acid molecules encoding a wild type gangliosidase and/or a sialidase or glucocerebrosidase, and any sequences which hybridize under standard conditions to these sequences. In another non-limiting embodiment, any other nucleotide sequence that encodes a gangliosidase and/or a sialidase or a glucocerebrosidase polypeptide (having the same functional properties and binding affinities as the aforementioned polypeptide sequences), such as allelic variants in normal individuals, that have the ability to achieve a functional conformation in the ER, achieve proper localization within the cell, and exhibit wild-type activity.

As used herein the term "mutant" gangliosidase and/or a sialidase or glucocerebrosidase refers to a gangliosidase and/or a sialidase or glucocerebrosidase polypeptide translated from a gene containing a genetic mutation that results in an altered gangliosidase and/or a sialidase or glucocerebrosidase amino acid sequence. In one embodiment, the mutation results in a gangliosidase and/or a sialidase or glucocerebrosidase protein that does not achieve a native conformation under the conditions normally present in the ER, when compared with wild-type gangliosidase and/or a sialidase or glucocerebrosidase, or exhibits decreased stability or activity as compared with a wild-type gangliosidase and/or sialidase or glucocerebrosidase. This type of mutation is referred to herein as a "conformational mutation," and the protein bearing such a mutation is referred as a "conformational mutant." The failure to achieve this conformation results in a gangliosidase and/or a sialidase or glucocerebrosidase protein being degraded or aggregated, rather than being transported through a normal pathway in the protein transport system to its native location in the cell or into the extracellular environment. In some embodiments, a mutation may occur in a non-coding part of the gene encoding a gangliosidase and/or a sialidase or glucocerebrosidase that results in less efficient expression of the protein, e.g., a mutation that affects transcription efficiency, splicing efficiency, mRNA stability, and the like. By enhancing the level of expression of wild-type as well as conformational mutant variants of a gangliosidase and/or a sialidase or glucocerebrosidase, administration of a gangliosidase and/or a sialidase or glucocerebrosidase pharmacological chaperone can ameliorate a deficit resulting from such inefficient protein expression.

Certain tests may evaluate attributes of a protein that may or may not correspond to its actual in vivo activity, but nevertheless are appropriate surrogates of protein functionality, and wild-type behavior in such tests demonstrates evidence to support the protein folding rescue or enhancement techniques of the invention. One such activity in accordance with the invention is appropriate transport of a functional a gangliosidase and/or a sialidase from the endoplasmic reticulum to the cytosol.

The terms "endogenous expression" and "endogenously expressed" refers to the normal physiological expression of a gangliosidase and/or a sialidase or glucocerebrosidase in cells in an individual not having or suspected of having a disease or disorder associated with gangliosidase and/or sialidase or glucocerebrosidase deficiency, overexpression of a dominant negative mutant, or other defect, such as a mutation in a gangliosidase and/or a sialidase or glucocerebrosidase nucleic acid or polypeptide sequence that alters, e.g., inhibits, its expression, activity, or stability. This term also refers to the expression of a gangliosidase and/or a sialidase or glucocerebrosidase in cells or cell types in which it is normally expressed in healthy individuals, and does not include expression of a gangliosidase and/or a sialidase or glucocerebrosidase in cells or cell types, e.g., tumor cells, in which a gangliosidase and/or a sialidase or glucocerebrosidase is not expressed in healthy individuals.

As used herein, the term "elevated ganglioside" refers to an individual, patient or patient population having increased ganglioside levels in the brain. The ganglioside levels may be elevated in the membranes throughout the cell and also within microdomains. The term "microdomains" or "lipid rafts" refers to detergent resistant areas found within cell membranes that are enriched in cholesterol, glycosphingolipids and gangliosides. In one aspect of this invention, pharmacological chaperones are used to decrease ganglioside levels in microdomains or lipid rafts by increasing the activity of enzymes known to catabolize gangliosides in the brain.

As used herein, the term "efficiency of transport" refers to the ability of a protein to be transported out of the endoplasmic reticulum to its native location within the cell, cell membrane, or into the extracellular environment.

A "competitive inhibitor" of an enzyme can refer to a compound which structurally resembles the chemical structure and molecular geometry of the enzyme substrate to bind the enzyme in approximately the same location as the substrate. Thus, the inhibitor competes for the same active site as the substrate molecule, thus increasing the Km. Competitive inhibition is usually reversible if sufficient substrate molecules are available to displace the inhibitor, i.e., competitive inhibitors can bind reversibly. Therefore, the amount of enzyme inhibition depends upon the inhibitor concentration, substrate concentration, and the relative affinities of the inhibitor and substrate for the active site.

Non-classical competitive inhibition occurs when the inhibitor binds remotely to the active site of an enzyme, creating a conformational change in the enzyme such that the substrate can no longer bind to it. In non-classical competitive inhibition, the binding of substrate at the active site prevents the binding of inhibitor at a separate site and vice versa. This includes allosteric inhibition.

A "linear mixed-type inhibitor" of an enzyme is a type of competitive inhibitor that allows the substrate to bind, but reduces its affinity, so the Km is increased and the Vmax is decreased.

A "non-competitive inhibitor" refers to a compound that forms strong bonds with an enzyme and may not be displaced by the addition of excess substrate, i.e., non-competitive inhibitors may be irreversible. A non-competitive inhibitor may bind at, near, or remote from the active site of an enzyme or protein, and in connection with enzymes, has no effect on the Km but decreases the Vmax. Uncompetitive inhibition refers to a situation in which inhibitor binds only to the enzyme-substrate (ES) complex. The enzyme becomes inactive when inhibitor binds. This differs from non-classical competitive inhibitors which can bind to the enzyme in the absence of substrate.

The term "Vmax" refers to the maximum initial velocity of an enzyme catalyzed reaction, i.e., at saturating substrate levels. The term "Km" is the substrate concentration required to achieve ½ Vmax.

An enzyme "enhancer" is a compound that binds to a gangliosidase and/or a sialidase and increases the enzymatic reaction rate.

The terms "therapeutically effective dose" and "effective amount" refer to an amount sufficient to enhance protein processing in the ER (permitting a functional conformation), without inhibiting protein already expressed at the appropriate cellular location (in the case of an antagonist), or without inducing ligand-mediated receptor internalization of protein from the appropriate cellular location (in the case of an agonist), and enhance activity of the target protein, thus resulting in a therapeutic response in a subject. A therapeutic response may be any response that a user (e.g., a clinician) will recognize as an effective response to the therapy, including the foregoing symptoms and surrogate clinical markers. Thus, a therapeutic response will generally be an amelioration or inhibition of one or more symptoms of a disease or disorder, e.g., Alzheimer's disease.

The phrase "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or any vehicle with which the compound is administered. Such pharmaceutical carriers, for example, can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an mRNA band on a gel, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acids include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material, such as a gangliosidase and/or a sialidase nucleic acid or polypeptide that has been isolated under conditions that reduce or eliminate unrelated materials, i.e., contaminants. For example, a purified protein is preferably substantially free of other proteins or nucleic acids with which it is associated in a cell. As used herein, the term "substantially free" is used operationally, in the context of analytical testing of the material. Preferably, purified material substantially free of contaminants is at least 50% pure; more preferably, at least 90%) pure, and more preferably still at least 99% pure. Purity can be evaluated by conventional means, e.g., chromatography, gel electrophoresis, immunoassay, composition analysis, biological assay, and other methods known in the art.

The term "tauopathy" refers to any condition resulting from the pathological aggregation of tau protein forming neurofibrillary tangles (NFT) in the human brain and includes (but is not limited to) diseases such as frontotemporal dementia, Alzheimer's disease, progressive supranuclear palsy, corticobasal degenerations and frontotemporal lobar degeneration (Pick's disease).

The term "cerebral amyloidosis" refers to a condition in which there is a deposition or accumulation of amyloid in the brain or in the blood vessels in the brain Examples of cerebral amyloidoses include, but are not limited to, Alzheimer's disease and cerebral amyloid angiopathy (CAA).

The term "Alzheimer's disease" or "AD" refers to a condition characterized by slowly progressive dementia and gross cerebral cortical atrophy. The presence of β-amyloid neuritic plaques, intra neuronal neurofibrillary tangles, and amyloid angiopathy are hallmarks of AD and are observed at postmortem examination. AD may be heritable in a Familial manifestation, or may be sporadic. Herein, AD includes Familial, Sporadic, as well as intermediates and subgroups thereof based on phenotypic manifestations. Familial AD typically has an early-onset (before age 65) while Sporadic AD typically is late-onset (age 65 and later). In a non-limiting embodiment, Familial AD may be associated with mutations in one or more genes selected from the group comprising presenilin 1 (human presenilin 1, GenBank Accession Nos. NM_000021, NM_007318, and NM_007319; murine presenilin 1, GenBank Accession No. NM 008943; and rat presenilin 1, GenBank Accession No. NM_019163), presenilin 2 (human presenilin 2, GenBank Accession Nos. NM_000447, and NM_012486; murine presenilin 2, GenBank Accession No. NM_011183; and rat presenilin 2, GenBank Accession No. NM 031087), and Amyloid Precursor Protein (APP) (human APP, GenBank Accession Nos. NM_201414, NM_201413, and NM 000484; murine APP, GenBank Accession No. NM 007471; and rat APP, GenBank Accession No. NM_019288). Sporadic AD cannot be tested for directly, but certain risk factors may increase an individual's susceptibility to developing sporadic AD. In one, non-limiting embodiment, individuals with at least one copy of the e4 allele of Apolipoprotein E (APOE) (human APOE, GenBank Accession No. NM 000041; murine APOE, GenBank Accession No. NM 009696; and rat APOE, GenBank Accession No. NM_138828) are at risk of developing late-onset sporadic AD.

This term also includes individuals with trisomy 21, or Down syndrome (DS), develop dementia that is identical to the clinical and neurophathogic characteristics of AD (in their third or fourth decade), including cerebral amyloid (Aβ) plaques and neurofibrillary tangles (NFTs), the characteristic lesions of Alzheimer disease (AD). Recent studies have shown that the Aβ42 is the earliest form of this protein deposited in Down syndrome brains, and may be seen in subjects as young as 12 years of age, and that soluble Aβ can be detected in the brains of DS subjects as early as 21 gestational weeks of age, well preceding the formation of Aβ plaques. Gyure et ah, Archives of Pathology and Laboratory Medicine 125: 489-492 (2000).

For purposes of the present invention, a "neurological disorder" refers to any central nervous system (CNS) or peripheral nervous system (PNS) disease that is associated with the β-amyloidogenic processing of Amyloid Precursor Protein (APP). This may result in neuronal or glial cell defects including but not limited to neuronal loss, neuronal degeneration, neuronal demyelination, gliosis {i.e., astrogliosis), or neuronal or extraneuronal accumulation of aberrant proteins or toxins {e.g., amyloid-β).

One exemplary neurological disorder is cerebral amyloid angiopathy (CAA) also referred to as congophilic angiopathy. This disorder is a form of angiopathy in which the same amyloid protein that is associated with Alzheimer's disease, amyloid-β (Aβ), deposits in the walls of the leptomeninges and superficial cerebral cortical blood vessels of the brain. Amyloid deposition predisposes these blood vessels to failure, increasing the risk of a hemorrhagic stroke. Since it is the same amyloid protein that is associated with Alzheimer's dementia, such brain hemorrhages are more common in people who suffer from Alzheimer's, however they can also occur in those who have no history of dementia. The hemorrhage within the brain is usually confined to a particular lobe and this is slightly different compared to brain hemorrhages which occur as a consequence of high blood pressure (hypertension)—a more common cause of a hemorrhagic stroke (or cerebral hemorrhage). CAA is also associated with transient ischemic attacks, subarachnoid hemorrhage, Down syndrome, post irradiation necrosis, multiple sclerosis, leucoencephalopathy, spongiform encephalopathy, and dementia pugilistica. Exemplary forms of CAA that may be treated according to embodiments of the present invention include hereditary CAA (also known as familial CAA) and hereditary cerebral hemorrhage with amyloidosis-Dutch type (HCHWA-D). In some embodiments, the hereditary CAA is caused by mutations in APP.

The term "individual" "patient" or "patient population" refers to a person(s) diagnosed as having or at risk of developing one of the various diseases described herein. For instance, the individuals may be diagnosed, or at risk of developing, Familial AD. In another instance, the individual is diagnosed as having, or at risk of developing, Sporadic AD. Diagnosis of AD may be made based on genotypic or phenotypic characteristics displayed by the individual. For example, an individual with a mutant variant of presenilin 1, presenilin 2, or APP are at risk of developing familial AD. In another, non-limiting example, individuals with the E4 variant of APOE are at risk for developing Sporadic AD.

An individual may be diagnosed as having AD, or at risk of developing AD, by exhibiting phenotypes associated with AD. Phenotypes associated with AD may be cognitive or psychiatric. Examples of cognitive phenotypes include, but are not limited to, amnesia, aphasia, apraxia and agnosia. Examples of psychiatric symptoms include, but are not limited to, personality changes, depression, hallucinations and delusions. As one non-limiting example, the Diagnostic and Statistical Manual of Mental disorders, 4th Edition (DSM-IV-TR) (published by the American Psychiatric Association) contains the following set of criteria for dementia of the Alzheimer's type:

A. The development of multiple cognitive deficits manifested by both memory impairment and one or more of Aphasia, Apraxia, Agnosia and disturbances in executive functioning;

B. The cognitive deficits represent as decline from previous functioning and cause significant impairment in social or occupational functioning;

C. The course is characterized by gradual onset and continuing decline;

D. The cognitive deficits are not due to other central nervous system, systemic, or substance-induced conditions that cause progressive deficits in memory and cognition; and E. The disturbance is not better accounted for by another psychiatric disorder.

Another non-limiting example is The National Institute of Neurological and Communicative Disorders and Stroke-Alzheimer's disease and Related Disorder Association (NINDS-ADRDA) Criteria for Alzheimer's disease as follows:

A. Definite Alzheimer's disease: meets the criteria for probable Alzheimer's disease and has histopathologic evidence of Alzheimer's disease via autopsy or biopsy B. Probable Alzheimer's disease: dementia established by clinical and neuropsychological examination and involves
  (a) progressive deficits in two or more areas of cognition, including memory,
  (b) onset between the ages of 40 and 90 years, and
  (c) absence of systemic or other brain diseases capable of producing a dementia syndrome, including delirium C. Possible Alzheimer's disease: a dementia syndrome with an atypical onset, presentation, or progression and without a known etiology; any co-morbid diseases capable of producing dementia are not believed to be the cause D. Unlikely Alzheimer's disease: a dementia syndrome with any of the following: sudden onset, focal neurologic signs, or seizures or gait disturbance early in the course of the illness.

Phenotypic manifestations of AD may also be physical, such as by the direct (imaging) or indirect (biochemical) detection of amyloid-β plaques. Quantitation of amyloid-β (1-40) in the peripheral blood has been demonstrated using high-performance liquid chromatography coupled with tandem mass spectrometry in a linear ion trap (Du et ah, J Biomol Tech. 16(4):356-63 (2005). Detection of single β-amyloid protein aggregates in the cerebrospinal fluid of Alzheimer's patients by fluorescence correlation spectroscopy also has been described (Pitschke et ah, Nature Medicine 4: 832-834 (1998). U.S. Pat. No. 5,593,846 describes a method for detecting soluble amyloid-β. Indirect detection of amyloid-β peptide and receptor for advanced glycation end products (RAGE) using antibodies also has been described. Lastly, biochemical detection of increased BACE-1 activity in cerebrospinal fluid using chromogenic substrates also has been postulated as a diagnostic or prognostic indicator of AD (Verheijen et al, Clin Chem. April 13 [Epub.] (2006).

In vivo imaging of β-amyloid can be achieved using radioiodinated flavone derivatives as imaging agents, Ono et al, J Med Chem. 48(23):7253-60 (2005), and with amyloid binding dyes such as putrescein conjugated to a 40-residue radioiodinated A peptide (yielding $^{125}$I-PUT-A 1-40), which was shown to cross the blood-brain barrier and bind to αβ plaques. Wengenack et al, Nature Biotechnology. 18(8):868-72 (2000). Imaging of β-amyloid was also shown using stilbene SB-13 and the benzothiazole 6-OH-BTA-1 (also known as PIB). Nicholaas et al, Am J Geriatr Psychiatry, 12:584-595 (2004).

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1

AdDNJ Crosses the BBB and Increases β-Hex without Affecting Viability

In order to evaluate the β-hex-targeted pharmacological chaperone AdDNJ as a therapeutic strategy to treat Dutch APP$^{E693Q}$ transgenic mice, we first performed studies to assess target engagement and effects on cellular viability. Also, in order to determine the appropriate doses and dosing regimens to use in our Dutch APP$^{E693Q}$ transgenic mouse proof-of-concept (POC) study, we completed pharmacokinetic and dose response/time course studies for AdDNJ using C57Bl6 mice. The objectives of the pharmacokinetic and dose response/time course studies were to confirm that AdDNJ crosses the blood brain barrier (BBB) and to determine the minimum dose and minimum duration of daily dosing that provides the largest increase in brain levels of endogenous wild-type β-hex in C57BL/J6 mice, while allowing AdDNJ to intermittently drop below inhibitory concentrations to enable disassociation from β-hex and the turnover of substrate.

Materials and Methods
AdDNJ Effect on Cell Viability.

Viability of human fibroblast (CRL2076) and human neuroblastoma (SH-SY5Y) cells was tested after prolonged exposure to varying concentrations of AdDNJ. In a 96-well plate, fibroblasts were incubated in complete media containing increasing concentrations of AdDNJ up to 1 mM for either 72 or 120 hours at 37° C. in a humidified 8% $CO_2$ incubator. Living cells were quantified using a tetrazoliuimformazan conversion method according to the manufacturer's instructions (Promega Non-Radioactive 96-well Titer assay, TB112). SH-SY5Y cells were tested in the same manner as fibroblasts but plated in collagen-coated plates (Nunc #152036). After 24 hour, 48 hour and 120 hour exposure to AdDNJ, living SH-SY5Y cells were quantified as described above. All dosing concentrations were done in triplicate.

Enzymatic Activities and AdDNJ Selectivity.

AdDNJ selectivity was assessed by measuring its effect on the enzymatic activity of hexosaminadase (Total Hex, Hex A/S and Hex B), and 3 other lysosomal hydrolases: alpha-galactosidase, beta-galactosidase and glucocerebrosidase. For enzymatic assays, wild-type fibroblast (CRL2076) pellets (~2.5e6 cells/pellet) were lysed with 200 µl of pH 5 lysis buffer (Phosphate/citrate, 0.25% tauorocholate, 0.1% TX100). Fibroblast lysates were diluted 1:200 in pH 5 reaction buffer (lysis buffer without TX100) containing 2 mM of the appropriate 4-methylumbelliferyl (4-MU) substrate, incubated for 1 h at 37° C. and stopped with 0.5 M sodium carbonate. Released 4MU was measured using a Perkin Elmer Victor 5× fluorescence plate reader (ex355/em460). Measurement of Total Hex activity was carried out using 4-methylumbelliferyl beta-N-acetylglucosaminide (MUG); for Hex A/S activity 4MU-beta-N-acetylglucosamine-6-sulfate (MUGS); Hex B activity was calculated as the difference between Total Hex and Hex A/S activity; for alpha-galactosidase activity 4MU-alpha-D-glucopyranoside; for beta-galactosidase activity 4-MU beta-D-galactoside; for glucocerebrosidase activity 4MU beta-D-glucopyranoside. As positive controls for enzymatic inhibition 100 µM of the following compounds were used: for alpha-galactosidase, 1-deoxygalactonojirimycin; for beta-galactosidase, N-Butyl-1-deoxygalactonojirimycin; for glucocerebrosidase, isofagamine. For beta-hexosaminadase enhancement assays, fibroblasts were exposed to 0, 95, 390 and 780 nM of AdDNJ for 5 days followed by beta-hexosamindase activity measurement. Enzymatic activity measurements were done in duplicate.

AdDNJ Effect on O-GlcNAcase Activity.

Effect of AdDNJ on cellular O-GlcNAcase activity was tested in both wild-type fibroblast (AG07059, Coriell) and SH-SY5Y cells. Fibroblasts were incubated with or without 10 µM AdDNJ or Thiamet G in complete media for 24 h at 37° C. in a humidified 8% $CO_2$ incubator. For SH-SY5Y cells, multiple concentrations (0 µM to 100 µM) of AdDNJ and Thiamet G were used. Cell pellets were lysed in RIPA buffer and total protein-associated O-GlcNAc level was measured using Western blot. Briefly, 40 µg total protein was separated, transferred to PVDF and probed with an anti O-GlcNAc antibody (18B10.C7, Pierce). Chemiluminescence was imaged using an Alpha Innotech FluoroChem Q imager and quantified by densitometry using AlphaView SA software (Alpha Innotech). The blots were stripped and re-probed with an anti-calnexin antibody (ab22595, Abcam). For O-GlcNAc quantification, whole lane O-GlcNAc densitometry was background subtracted and normalized to the calnexin load control band.

AdDNJ Repeat Dose/Dose-Response and PK Studies.

5-week-old C57BL/J6 mice (n=5 mice/group, Taconic Farms, Germantown, N.Y.) were administered vehicle (water) or AdDNJ (30, 100 or 300 mg/kg) via oral gavage every day for 14 days. On day 15 mice were euthanized and brain/plasma collected for analysis. For single dose PK studies, 5-week-old C57BL/J6 mice (n=5 mice/group, Taconic Farms, Germantown, N.Y.) received a single 100 mg/kg dose (oral gavage) of AdDNJ and groups euthanized at 0.5, 1, 2, 4, 8, 16, 24 and 48 hours post dose for brain and plasma analysis. Whole brain tissue (10-15 mg) was homogenized in 1 mL of pH 5 lysis buffer for measuring beta-hexosaminidase activity as described above. AdDNJ levels were measured in plasma and brain samples using LC-MS/MS.

Results

AdDNJ was a potent and specific inhibitor of β-hex (Ki=253.4 nM at pH 5; Ki=342.3 nM at pH 7; FIG. 1 a) and did not inhibit O-GlcNAcase (FIGS. 1 c-d) at concentrations up to 100 μM or the lysosomal enzymes β-glucocerebrosidase (GCase), α-galactosidase (α-Gal), or β-galactosidase (β-Gal) at 10 μM, the highest concentration tested (FIG. 1 e). Additionally, AdDNJ had little or no effect on cell viability for SH-SY5Y and human skin fibroblasts treated with concentrations as high as 1 mM AdDNJ for up to 120 hours (FIGS. 1 f-g). Treatment of healthy human skin fibroblasts for 5 days with 95, 390, or 780 nM AdDNJ increased β-hex levels in a dose-dependent manner by up to 3-fold (FIG. 1 b) demonstrating the ability of AdDNJ to engage its target β-hex.

Figure 10:
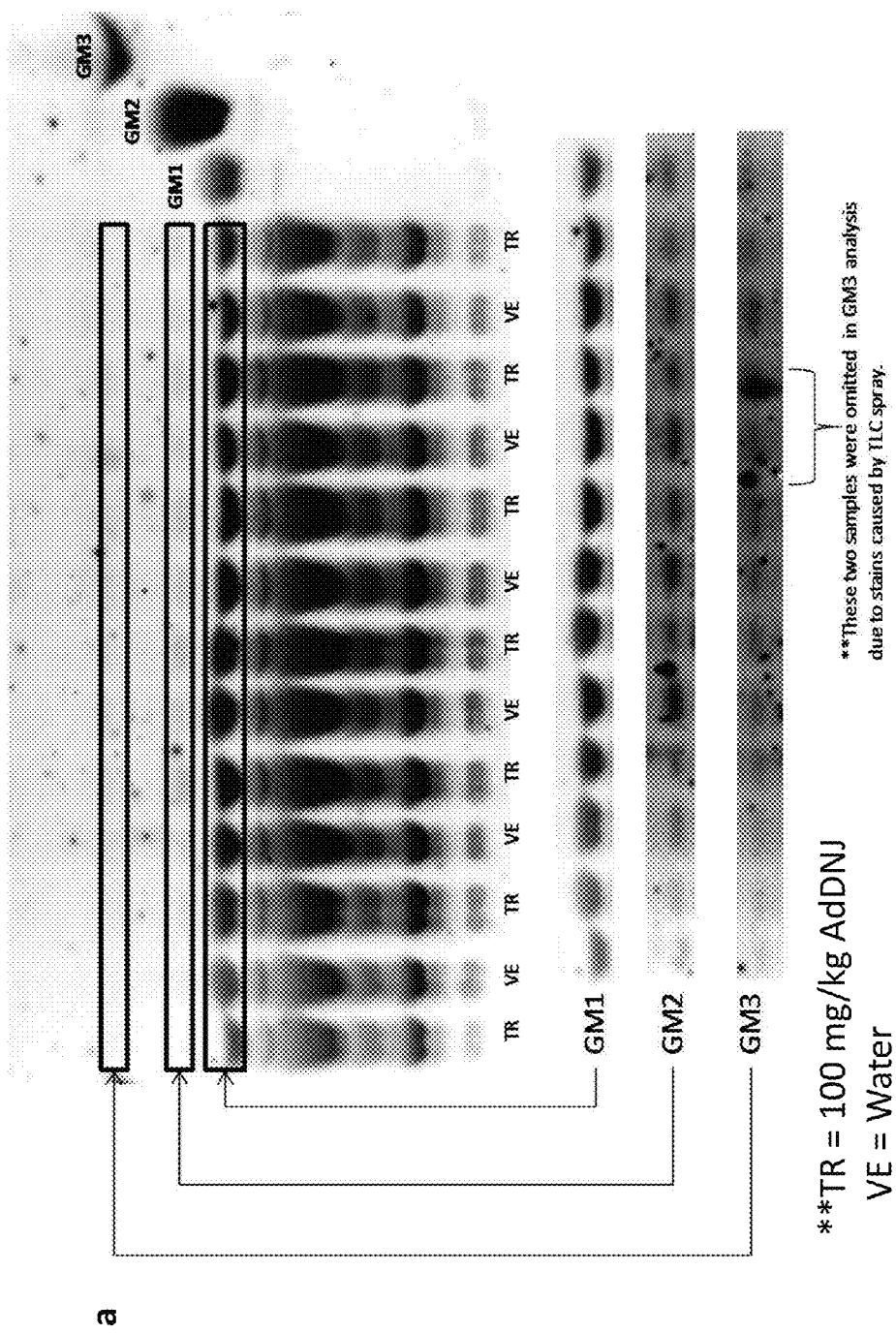
FIGS. 10 a-d show AdDNJ treatment of Dutch APP$^{E693Q}$ transgenic mice has no detectable effect on ganglioside profiles as assessed by TLC. 3-month-old male Dutch transgenic mice were either untreated, or orally dosed with vehicle or AdDNJ for three months. Thin-layer chromatography analysis of whole forebrain revealed that AdDNJ treatment does not significantly alter GM1, GM2, and GM3 ganglioside levels (a-d) (vehicle; n=6, 100 mg/kg AdDNJ; n=7).

In single dose (oral gavage) pharmacokinetic studies, we found that a 100 mg/kg dose of AdDNJ crossed the BBB and reached levels in the brain that are predicted to be sufficient to favor binding of β-hex in the neutral pH environment of the ER (342 nM, AdDNJ's Ki for β-hex inhibition at pH 7) and dropped below levels predicted to inhibit lysosomal β-hex (i.e., 253 nM, AdDNJ's Ki for β-hex inhibition at pH 5) within 16 hours (FIGS. 2 a-b). Additionally, daily dosing of AdDNJ for 14 days at 30,100, and 300 mg/kg via gavage demonstrated a dose-dependent increase in β-hex levels (FIGS. 3 a-b), without increasing GM2 levels in whole brain extracts (FIGS. 10 a and c). At these doses, the maximum increase in β-hex levels occurred at ~5 days of treatment (FIGS. 3 a-b). Since the half-life of elevated β-hex levels in the brain was ~2 days (data not shown), we chose the treatment strategy of treating mice once daily for 5 days to maximize β-Hex enhancement followed by 2 days without drug (to maximize substrate turnover in the absence of AdDNJ). All doses were well tolerated by mice.

Example 2

AdDNJ Proof-of-Concept Study

Next we performed a POC study to evaluate whether AdDNJ reduces ganglioside-bound Aβ pathology in Dutch APP$^{E693Q}$ transgenic mice.

Animals and Study Design.

The generation and characterization of Dutch APPE693Q mice transgenic mice is described in Gandy, S., et al. Days to criterion as an indicator of toxicity associated with human Alzheimer amyloid-beta oligomers. *Annals of neurology* 68, 220-230 (2010). 3-month-old male Dutch APP$^{E693Q}$ mice transgenic mice were orally gavaged 5 days/week with either vehicle (water) (n=15) or 3, 10, 30 or 100 mg/kg AdDNJ for 3 months (n=13). All animal studies were approved and conducted in accordance with the Institutional Animal Care and Usage Committee. Mice were kept in a pathogen-free environment, on a 12-hour light/dark cycle and given ad libitum access to food and water. At 6 month of age treatment groups, and a 3-month-old untreated baseline group (n=15), were cognitively assessed in the NOR, EPM and FC tests. 48 hours following the final dose mice were perfused with ice-cold 1×PBS. The brain was removed and dissected into two hemispheres. One half was snap-frozen on dry ice and stored at −80° C. for biochemistry; the other half was post-fixed in 4% paraformaldehyde then sagittally sectioned on a vibratome into 30 μm sections and stored at 4° C. in storage buffer until histological analyses.

Behavioral Testing.

Mice were placed in the testing room 1 hour prior to testing to acclimatize mice to the room. All testing was completed between 8 am-3 pm Tuesday-Friday two weeks prior to final dosing of AdDNJ. All equipment was cleaned between animals.

Novel Object Recognition (NOR).

On day 1, the mouse was placed in the NOR arena (20 cm diameter) for 10 min to acclimatize. On day 2, the mouse underwent the testing phase, composed of two stages. During testing phase 1, the mouse was placed in the arena and allowed to explore two identical unfamiliar objects for 10 minutes. The mouse was then returned to their home cage for an interval of 1 hour. During this time, one of the two objects the mouse was previously allowed to explore was removed and replaced with a novel object. During testing phase 2, the mouse was placed back into the arena and allowed to explore the familiar object and the novel object for 4 min. Trials were videotaped using an overhead camera. The duration spent exploring the objects was then measured using ANY-maze (Stoelting, Wood Dale, Ill.).

Elevated Plus Maze (EPM).

The maze in the configuration of a+ and comprised two open arms (35×5×0 cm) across from each other and perpendicular to two closed arms (35×5×16 cm) with a central neutral zone (Stoelting, Wood Dale, Ill.). The mouse was placed in the neutral zone and allowed to explore for 8 minutes. Each trial was videotaped overhead and scored for amount of time spent in the open and closed arms using ANY-maze (Stoelting, Wood Dale, Ill.). Entry into an arm was defined as having head and two paws into arms.

Fear Conditioning.

Contextual and cued fear conditioning was assessed using the ANY-Maze fear conditioning system (Stoelting Co., Wood Dale, Ill., USA) as previously described in Steele, J. W., et al. Early fear memory defects are associated with altered synaptic plasticity and molecular architecture in the TgCRND8 Alzheimer's disease mouse model. *The Journal of comparative neurology* (2014).

Aβ Assay.

Right hemibrains were processed via differential detergent solubilizationin accordance with Kawarabayashi, T., et al. Age-dependent changes in brain, CSF, and plasma amyloid (beta) protein in the Tg2576 transgenic mouse model of Alzheimer's disease. *J Neurosci* 21, 372-381 (2001). For analysis of native oligomeric Aβ protein structure, 2-4 μL native protein samples from TBS-soluble were spotted onto activated/pre-wetted PVDF membrane (0.22 μm; Millipore) and allowed to dry. Following protein spotting, membranes were blocked for 1 h at room temperature in 5% w/v non-fat milk (Santa Cruz) in TBS containing 0.1% v/v Tween-20 (Fisher Scientific; TBS-T). Membranes were then incubated in the indicated primary antibody (in 5% milk/TBS-T) overnight at 4 C, washed 4× in TBS-T, incubated in species-specific HRP-conjugated secondary antibody (in 5% milk/TBS-T) for 1 h at room temperature, and then washed 4× in TBS-T. Membranes were subsequently developed with ECL Western blotting substrate (Pierce) using the Fujifilm LAS-3000 developer. Membranes were then washed 1× in TBS-T and stripped in low pH stripping buffer [25 mM Glycine HCl, pH 2.0 and 1% w/v SDS] with vigorous shaking to remove primary and secondary antibody, washed 3× in TBS-T, and blocked for 1 h (in 5% milk/TBS-T) at room temperature before probing with the next primary antibody. Integrated density of immunoreactive spots was measured using MultiGauge Software (FujiFilm) and normalized to % control (vehicle). Generation, purification, and characterization of rabbit pAβ A11 (anti-prefibrillar oligomers, 0.5 μg/ml), rabbit pAβ OC (anti-fibrillar oligomers and fibrils; 0.25 μg/ml) and mouse mAβ Nu-4 (anti-oligomers; 1 μg/ml) have been described previously (Tomic, J. L., Pensalfini, A., Head, E. & Glabe, C. G. Soluble fibrillar oligomer levels are elevated in Alzheimer's disease brain and correlate with cognitive dysfunction. Neurobiology of disease 35, 352-358 (2009); Lambert, M. P., et al. Monoclonal antibodies that target pathological assemblies of Abeta. Journal of neurochemistry 100, 23-35 (2007)). Normalization to total APP/Aβ signal was achieved by detection of human APP transgene metabolites with the mouse mAb 6E10 (1:1000; Covance). Peroxidase-conjugated goat anti-rabbit IgG (H+L; 1:20,000; Vector Labs) or goat anti-mouse IgG (H+L; 1:20,000; Vector Labs) were used for detection. To quantify monomeric Aβ levels, human/rat Aβ 1-40/1-42 ELISA kits (Wako) were used according to the manufacturer's instructions. Absolute concentrations of monomeric or oligomeric Aβ were normalized to initial tissue weight prior to analysis.

Histology.

Aβ was assessed via free-floating immunohistochemistry using mAb 6E10 (1:1000, Covance) as previously described20. GAβ was assessed via free-floating immunohistochemistry using mouse anti-GAβ, clone 4396C (1:100), a gift from Dr. Katsuhiko Yanagisawa as previously described19. Images were captured on an Olympus BX61 upright microscope with an attached Olympus DP71 camera. Integrated density of GAβ staining was measured using Image J (National Institute of Health, Bethesda, Md.).

Statistical Analyses of Behavioral, Biochemical and Histological Outcomes.

All data are presented as the mean±s.e.m. Statistical significance (P<0.05) was determined using Student's t tests or one-way ANOVA with Bonferroni posthoc analyses (GraphPad Prism, San Diego, Calif.).

Results

AdDNJ Increased β-Hex Levels in Dutch APP$^{E693Q}$ Transgenic Mice

We wanted to assess whether AdDNJ engaged its target β-hex in Dutch APP$^{E693Q}$ transgenic mice. We observed that a 3-month course of AdDNJ increased total brain β-hex in a dose-dependent manner up to 3-fold at the highest dose (FIG. 4 c). AdDNJ also increased β-hex B (FIG. 4 a) and β-hex A&S (FIG. 4 b) in a dose-dependent manner. TLC analysis of whole brain extracts did not reveal any changes in ganglioside levels, indicating that β-hex was not generally inhibited throughout the brain even after 3 months of 100 mg/kg AdDNJ administration (FIGS. 10 a-d). Based on the proposed pharmacological chaperone mechanism of action for AdDNJ, we would expect to observe a decrease in GM2 gangliosides. However, the TLC analysis of FIGS. 10 a-d is not sensitive enough to show relatively small changes in ganglioside levels, though the TLC analysis would be expected to show the orders-of-magnitude increase in ganglioside levels that would be expected with sustained inhibition of β-hex. Furthermore regional changes could be masked since only whole brain homogenates were assessed. The most significant reductions in GAβ were observed for the subiculum and perirhinal cortex regions, which would account for a very small percentage of the total brain volume used to generate the homogenates.

AdDNJ Corrected the Behavioral Phenotype of Dutch APP$^{E693Q}$ Transgenic Mice

We assessed anxiety in the elevated plus maze (EPM) and observed that 6-month-old vehicle-treated Dutch APP$^{E693Q}$ transgenic mice were more anxious than 3-month-old untreated mice (FIG. 5 a). We observed that a 3-month course of AdDNJ was associated with reduced anxiety at all doses tested (FIG. 5 a).

Figure 6:
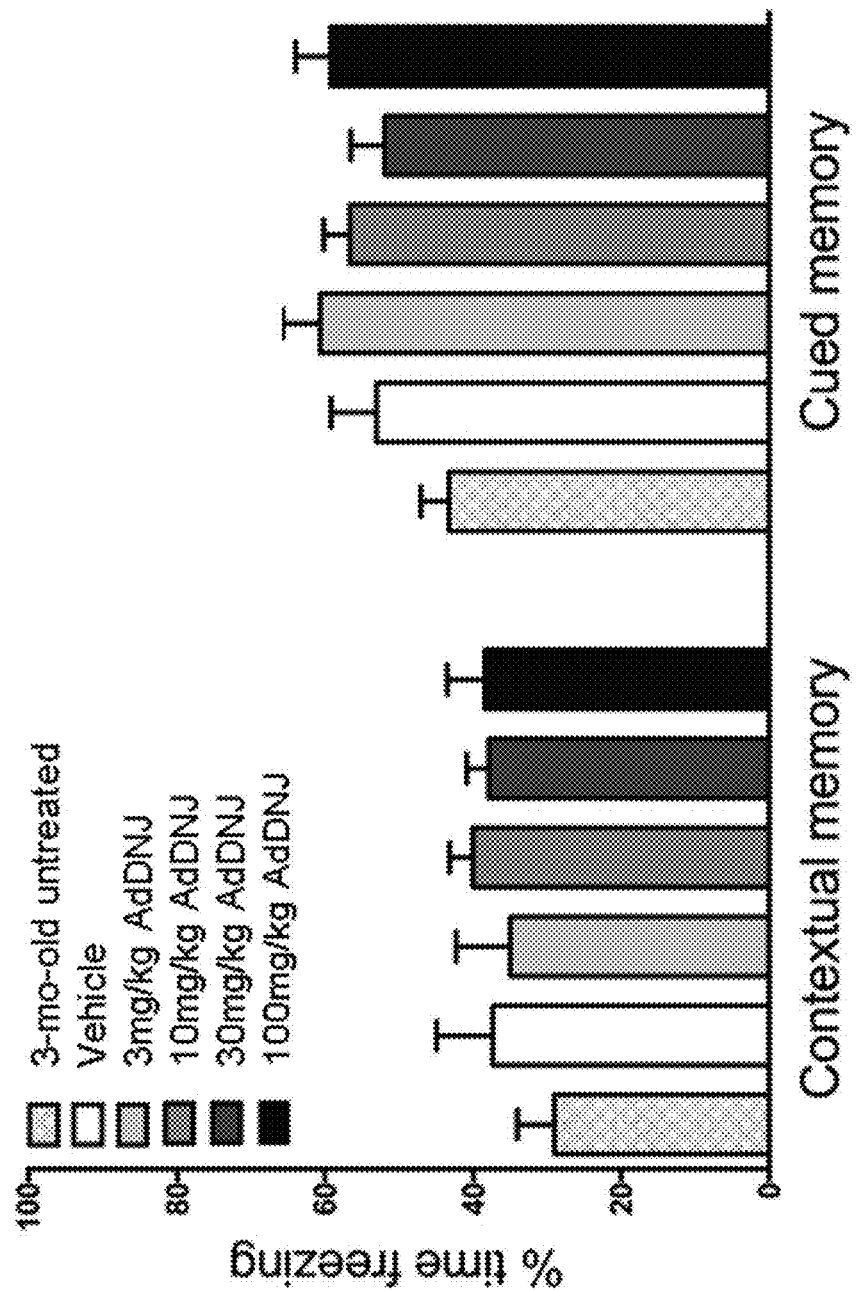
FIG. 6 shows contextual and cued fear conditioning learning behavior following treatment of AdDNJ in Dutch APP$^{E693Q}$ transgenic mice. 3-mo-old male Dutch APP$^{E693Q}$ transgenic mice were either untreated (n=15), or orally dosed with vehicle (n=15) or AdDNJ (3, 10, 30 or 100 mg/kg AdDNJ; treated n=13/group) for three months. AdDNJ had no effect on contextual or cued learning behavior. Data expressed as mean±s.e.m.

We assessed learning behavior by employing the novel object recognition (NOR) test. Three-month-old untreated Dutch APP$^{E693Q}$ transgenic mice displayed intact learning behavior as evidenced by their spending significantly more time exploring the novel object over the familiar object, whereas 6-month-old vehicle-treated mice exhibited learning behavior deficits (FIG. 5 b). Following a 3-month course of AdDNJ, we observed that same mice (now at 6 months of age) that showed reduced anxiety also showed protection from the typical aging-related learning behavior deficits in the NOR test at higher doses (FIG. 5 b). Six-month-old Dutch APP$^{E693Q}$ transgenic mice treated with AdDNJ at doses of 30 or 100 mg/kg displayed the learning behavior of mice half their age. In contrast, AdDNJ had no effect on contextual or cued fear conditioning (FIG. 6).

AdDNJ Reduced all and Ganglioside-Bound all Pathology in Dutch APP$^{E693}$Q Transgenic Mice Next, we assessed Aβ and ganglioside-bound Aβ (GAβ) in Dutch APP$^{E693Q}$ transgenic mice following 3-month treatment of AdDNJ. We found no change in Aβ40 (FIGS. 7 a-d), Aβ42 (FIGS. 7 e-h), Aβ42/40 ratio (FIGS. 7 i-l), prefibrillar Aβ (FIG. 7 m), or Aβ oligomer levels (FIGS. 7 n,o), at any dose of AdDNJ tested. We then went on to look for regional changes in Aβ and/or GAβ. Immunohistochemical analysis revealed a qualitative region-specific reduction of Aβ accumulation, specifically within the subiculum (FIGS. 8 a,b), however no differences were observed in the visual cortex (FIGS. 8 c,d) nor CA1 region of the hippocampus (FIGS. 8 e,f) of Dutch APP$^{E693Q}$ transgenic mice dosed with 100 mg/kg AdDNJ.

Region-specific reduction in Aβ was accompanied with a striking quantitative reduction in GAP within the subiculum (FIGS. 9 a,b,k) and perirhinal cortex (FIGS. 9 c,d,i) (areas in the brain involved in NOR). A trend toward reduction in GAβ was observed in the lateral entorhinal cortex (FIGS. 9 e,f,m), another brain region involved in NOR. A reduction in GAP did not reach significance in the visual cortex (FIGS. 9 g,h,n) or in the CA1 region of the hippocampus (FIGS. 9 l,j,o). GAβ-like immunoreactivity was also readily detectable in cortical blood vessels (FIG. 9 p).

Discussion

GM2 and GM3 gangliosides promote the assembly of a mutant form of Aβ (Dutch Aβ) that is highly susceptible to oligomerization in vitro (Yamamoto et al., 2005). GM2 and GM3 gangliosides are selectively expressed in the cerebrovasculature and have been shown to promote assembly of not only the Dutch mutant Aβ but also the Iowa-type and Italian-type mutant Aβ peptides, all of which underlie familial CAA (Yamamoto et al., 2005; Yamamoto et al., 2006). The convergence of ganglioside localization and the region-specific accumulation of mutant peptides susceptible to ganglioside-accelerated aggregation raise the possibility that these data have particular implications for familial CAA and AD. Dutch APP$^{E693Q}$ transgenic mice accumulate intraneuronal Aβ, which is observed in early stages of AD.

In this study, we demonstrated that the pharmacological chaperone AdDNJ crosses the BBB and causes increased levels of wild-type β-hex in the brains of wild-type C57BL/J6 mice. We then went on to assess the effect of AdDNJ on Aβ and GAβ deposition and onset of anxiety and learning behavioral deficits in Dutch APP$^{E693Q}$ transgenic mice. We confirmed that Dutch APP$^{E693Q}$ transgenic mice show aging-dependent deficits in anxiety and learning behavior, with age of onset of memory deficits at 6-month of age. Dutch APP$^{E693Q}$ transgenic mice had intact learning behavior in the NOR test at 3-month of age, whereas 6-month-old vehicle treated mice showed impaired learning behavior. The functional impairments observed in Dutch APP$^{E693Q}$ transgenic mice at 6-month of age were associated with Aβ accumulation, specifically within neurons in the subiculum, visual cortex and CA1 region of the hippocampus. These are regions of the brain we have previously demonstrated that Dutch mutant APP$^{E693}$ mice accumulate the most obvious aging-dependent Aβ deposition. The strongest Aβ-like immunoreactivity was observed in the subiculum. Recent studies have implicated the subiculum in memory, specifically in the NOR test in mice, where we see deficits in Dutch APP$^{E693Q}$ transgenic mice (Chang et al., 2012).

We have also observed that a β-hex-targeted pharmacological chaperone corrects two features of the behavioral phenotype of the Dutch APP$^{E693Q}$ transgenic mouse in association with an apparent reduction of Aβ and GAβ accumulation. A 3-month course of AdDNJ was associated with a 3-fold increase in β-hex levels in the brains of Dutch APP$^{E693}$ transgenic mice, demonstrating that AdDNJ was engaging its target. A striking quantitative reduction in GAβ was observed within the subiculum and perirhinal cortex, areas in the brain involved in NOR. A decrease in GAβ was also observed in the lateral entorhinal cortex, visual cortex and CA1 region of the hippocampus but did not reach statistical significance.

Our studies provide the first evidence that a β-hex-targeted pharmacological chaperone increases β-hex levels, while decreasing GAβ pathology in regions that demonstrate the highest amount of Aβ immunoreactivity. These molecular and histological changes occur in association with correction of two aspects of the behavioral phenotype (i.e., anxiety, learning behavior). These data highlight the potentially beneficial effect of increasing β-hex activity using a targeted pharmacological chaperone. This class of compound shows promise for mitigation of cerebral amyloidosis and is expected to be beneficial for management of the human cerebral amyloidoses, especially those associated with amyloid angiopathy and APP/Aβ mutations. AdDNJ has good bioavailability, BBB penetration, high selectivity for β-hex and low cytotoxicity making AdDNJ an excellent drug candidate, which could be quickly developed for clinical trials in patient populations with the Dutch APP mutation, making the results observed in Dutch APP$^{E693Q}$ transgenic mice particularly relevant.

What is claimed is:

1. A method for treating Alzheimer's disease or cerebral amyloid angiopathy in a patient diagnosed with the same, the method comprising:
   administering daily to the patient an effective amount of 2-acetamido-1,2-dideoxynojirimycin (AdDNJ) for a first enzyme enhancement period of about 1 day to about 8 days;
   not administering the AdDNJ for a substrate turnover period of about 48 hours to about 96 hours; and then
   administering to the patient an effective amount of AdDNJ for a second enzyme enhancement period of about 1 day to about 8 days.

2. The method of claim 1, wherein the first enzyme enhancement period and the second enzyme enhancement period have the same duration.

3. The method of claim 2, wherein one or more of the first enzyme enhancement period and the second enzyme enhancement period is a period of about 4 days to about 6 days.

4. The method of claim 1, wherein the AdDNJ is administered orally.

5. The method of claim 1, wherein the AdDNJ is administered at a dose in the range of about 3 mg/kg/day to about 300 mg/kg/day.

6. The method of claim 5, wherein the AdDNJ is administered at a dose of about 100 mg/kg/day.

7. The method of claim 6, wherein not administering the AdDNJ for the substrate turnover period comprises not administering AdDNJ for a period of about 72 hours.

8. A method for treating Alzheimer's disease or cerebral amyloid angiopathy in a patient diagnosed with the same, the method comprising:
   administering daily to the patient an effective amount of 2-acetamido-1,2-dideoxynojirimycin (AdDNJ) for a first enzyme enhancement period of about 5 days;
   not administering the AdDNJ for a substrate turnover period of about 72 hours; and then
   administering to the patient an effective amount of AdDNJ for a second enzyme enhancement period of about 1 day to about 8 days.

9. A method for treating Alzheimer's disease or cerebral amyloid angiopathy in a patient diagnosed with the same wherein the method comprises:
   administering to the patient an effective amount of AdDNJ on a first day;
   not administering the AdDNJ on a second day;
   administering to the patient an effective amount of AdDNJ on a third day;
   not administering the AdDNJ on a fourth day;
   administering to the patient an effective amount of AdDNJ on a fifth day; and then
   not administering the AdDNJ for a period of about 72 hours.

10. The method of claim 1, wherein not administering the AdDNJ for a substrate turnover period comprises not administering AdDNJ for a period of about 24 hours.

11. The method of claim 1, wherein not administering the AdDNJ for a substrate turnover period comprises not administering AdDNJ for a period of about 48 hours.

12. The method of claim 1, wherein the first enzyme enhancement period is about 3 days and not administering the AdDNJ for the substrate turnover period comprises not administering AdDNJ for a period of about 120 hours.

13. The method of claim 1, wherein the method comprises alternating between enzyme enhancement periods and substrate turnover periods for a total treatment time of at least 1 month.

14. The method of claim 13, wherein the total treatment time is at least 3 months.

15. The method of claim 13, wherein at least one substrate turnover period has a different duration than at least one other substrate turnover period.

16. A kit comprising:
   one or more active dosage forms comprising an effective amount of 2-acetamido-1,2-dideoxynojirimycin (AdDNJ);
   one or more inactive dosage forms that do not comprise an effective amount of AdDNJ; and
   instructions for:
   administering the dosage forms for a first enzyme enhancement period of about 1 day to about 8 days;

not administering the dosage forms for a substrate turnover period of about 48 hours to about 96 hours; and then
administering the dosage forms for a second enzyme enhancement period of about 1 day to about 8 days.

* * * * *